(12) United States Patent
Denyer et al.

(10) Patent No.: US 12,397,122 B1
(45) Date of Patent: Aug. 26, 2025

(54) MEDICAMENT DELIVERY DEVICE

(71) Applicant: Genzyme Corporation, Cambridge, MA (US)

(72) Inventors: Timothy Denyer, Melbourn (GB); James Bradford, Melbourn (GB); Alexander Hee-Hanson, Melbourn (GB); Robert Wilson, Melbourn (GB); Dean Twite, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/819,429

(22) Filed: Aug. 29, 2024

(51) Int. Cl.
| A61M 5/20 | (2006.01) |
| A61M 5/315 | (2006.01) |
| A61M 5/32 | (2006.01) |

(52) U.S. Cl.
CPC ........ *A61M 5/3204* (2013.01); *A61M 5/3243* (2013.01); *A61M 2005/208* (2013.01); *A61M 2005/3267* (2013.01)

(58) Field of Classification Search
CPC ................ A61M 5/3243; A61M 5/326; A61M 2005/3267; A61M 2005/208
See application file for complete search history.

(56) References Cited

U.S. PATENT DOCUMENTS

| 4,989,307 A | 2/1991 | Sharpe et al. |
| 5,069,667 A | 12/1991 | Freundlich et al. |
| 5,092,462 A | 3/1992 | Sagstetter et al. |
| 5,356,385 A | 10/1994 | Latini |
| 6,224,567 B1 | 5/2001 | Roser |
| 8,376,993 B2 | 2/2013 | Cox et al. |

(Continued)

FOREIGN PATENT DOCUMENTS

| FR | 2024089 A5 | 8/1970 |
| WO | WO 2014/060369 A1 | 4/2014 |

(Continued)

OTHER PUBLICATIONS

Needle-based injection systems for medical use requirements and test methods, Part 1: Needle injection systems, ISO 11608 1:2014(E), Third Edition, Switzerland, ISO, Dec. 15, 2014, pp. 1-13.

(Continued)

*Primary Examiner* — Laura A Bouchelle
(74) *Attorney, Agent, or Firm* — Fish & Richardson P.C.

(57) ABSTRACT

A medicament delivery device comprises: a needle for injecting a medicament; a body; a needle cover axially movable relative to the body between an extended position and a retracted position; a needle cover biasing member configured to bias the needle cover distally; a medicament delivery mechanism; and a latch movable by the needle cover between an engaged configuration, in which the latch prevents delivery of the medicament, and a disengaged configuration, in which the latch allows delivery of the medicament, wherein the needle cover is configured such that: proximal movement of the needle cover from the extended position towards the retracted position moves the latch from the engaged configuration to the disengaged configuration; and distal movement of the needle cover from the retracted position towards the extended position moves the latch from the disengaged configuration to the engaged configuration.

18 Claims, 16 Drawing Sheets

(56) References Cited

U.S. PATENT DOCUMENTS

| | | |
|---|---|---|
| 2013/0096513 A1 | 4/2013 | Smith |
| 2015/0265776 A1 | 9/2015 | Beek et al. |
| 2016/0129188 A1 | 5/2016 | Kiilerich |
| 2017/0246396 A1 | 8/2017 | Wei |
| 2020/0001014 A1 | 1/2020 | Holmqvist |
| 2021/0162137 A1 | 6/2021 | Hagihira et al. |
| 2021/0236714 A1 | 8/2021 | Limaye |
| 2022/0288299 A1 | 9/2022 | Limaye et al. |
| 2023/0001101 A1* | 1/2023 | Larsen ................ A61M 5/3202 |
| 2023/0277769 A1 | 9/2023 | Chang |
| 2025/0018119 A1 | 1/2025 | Lin et al. |
| 2025/0041529 A1 | 2/2025 | Kwolek et al. |

FOREIGN PATENT DOCUMENTS

| | | |
|---|---|---|
| WO | WO 2014/198858 A1 | 12/2014 |
| WO | WO 2018/146589 A2 | 8/2018 |
| WO | WO 2018/215271 A1 | 11/2018 |
| WO | WO 2021/122192 A1 | 6/2021 |
| WO | WO 2021/122196 A1 | 6/2021 |
| WO | WO 2022/023011 A1 | 2/2022 |
| WO | WO 2022/117671 A1 | 6/2022 |
| WO | WO 2022/117683 A1 | 6/2022 |
| WO | WO 2022/175241 A1 | 8/2022 |
| WO | WO 2022/175242 A1 | 8/2022 |
| WO | WO 2022/175245 A1 | 8/2022 |
| WO | WO 2022/175246 A1 | 8/2022 |
| WO | WO 2022/175247 A1 | 8/2022 |

OTHER PUBLICATIONS

U.S. Appl. No. 18/819,497, filed Aug. 29, 2024, Timothy Denyer.

* cited by examiner

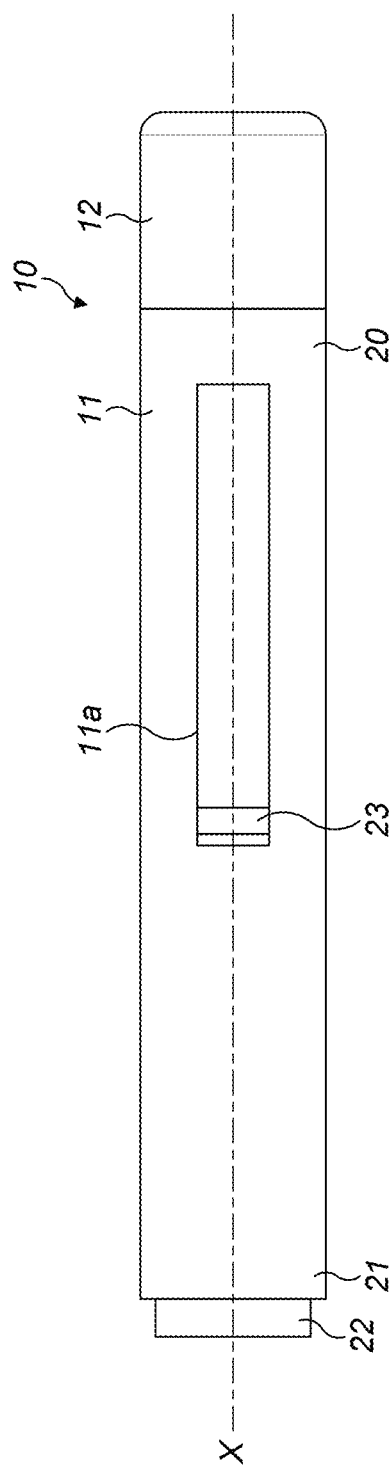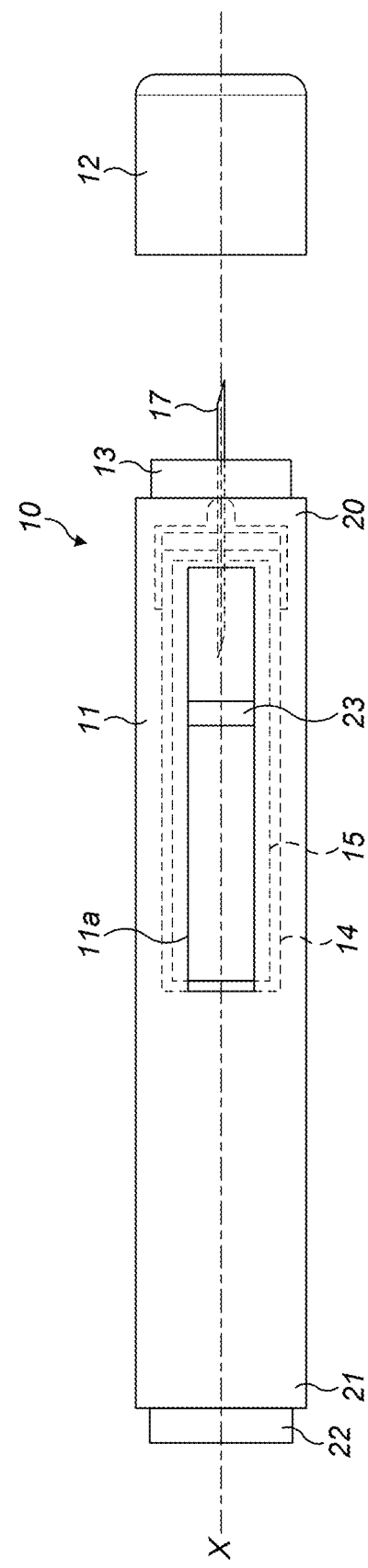

MEDICAMENT DELIVERY DEVICE

TECHNICAL FIELD

This application relates to a medicament delivery device for delivery of a medicament, and a method of using a medicament delivery device.

BACKGROUND

Drug delivery devices such as auto-injectors are used to deliver a range of medicaments. In an auto-injector device, some or all of the actions required to use the injector device in administering medicament are automated.

An auto-injector device may have a needle cover which is axially movable to cover and uncover a needle, with the needle cover being biased by a spring to extend over the needle. Typically, the user presses the needle cover against an injection site, against the force of the spring, to push the needle cover into the housing and to uncover the needle which is pushed into the injection site. Medicament is automatically dispensed from the needle via an automated mechanism. A user must typically hold the needle cover in a holding position for a predetermined period of time, to ensure that the correct dose of medicament is dispensed from the device, before removing the device from the injection site.

Some users may experience discomfort during the medicament delivery process. For example, some users may experience discomfort in the vicinity of the injection site when the delivered dose of medicament is large and/or delivered over a long period of time. If the discomfort becomes excessive, these users may decide to remove the auto-injector device from the injection site prematurely, which may result in incomplete delivery of the medicament dose, additional discomfort from premature withdrawal of the needle, and/or a wet injection site from leaked medicament.

The present disclosure provides an injector device that addresses one or more of the problems mentioned above, and to provide an improved injector device.

SUMMARY

A first aspect of this disclosure provides medicament delivery device comprising: a needle for injecting a medicament; a body having a proximal end and a distal end; a needle cover axially movable relative to the body between an extended position, in which a distal end of the needle cover is distal to a distal end of the needle, and a retracted position, in which the distal end of the needle is distal to the distal end of the needle cover; a needle cover biasing member configured to bias the needle cover distally; a medicament delivery mechanism; and a latch movable by the needle cover between an engaged configuration, in which the latch is engaged with a component of a medicament delivery mechanism to prevent delivery of the medicament, and a disengaged configuration, in which the latch is disengaged from the component of the medicament delivery mechanism to allow delivery of the medicament, wherein the needle cover is configured such that: proximal movement of the needle cover from the extended position towards the retracted position moves the latch from the engaged configuration to the disengaged configuration; and distal movement of the needle cover from the retracted position towards the extended position moves the latch from the disengaged configuration to the engaged configuration.

The latch may be movable between the engaged position and the disengaged position a plurality of times for pausing and resuming delivery of the medicament a plurality of times.

The medicament delivery device may further comprise a needle cover guide comprising a track, wherein the needle cover comprises an arm configured to engage the track such that a proximal movement of the needle cover is limited after the needle cover has moved from the retracted position to the extended position.

The needle cover guide may be rotatable relative to the body, wherein the track extends at least partially around a circumference of the needle cover guide for rotating the needle cover guide as the needle cover moves from the extended position to the retracted position.

The flexible arm may comprise a protrusion configured to engage the track.

The track may comprise a first region and a second region, wherein the protrusion travels from the first region to the second region as the needle cover moves from the extended position to the retracted position. The first region may extend at least partially around the circumference of the needle cover guide.

The track may further comprise a third region, the protrusion may travel from the second region to the third region as the needle cover moves distally from the retracted position to the extended position, and the third region may comprise a locking element configured to limit proximal movement of the needle cover when the needle cover is in the extended position.

The locking element may comprise a locking surface configured to be engaged by the needle cover when the needle cover is in the extended position to limit proximal movement of the needle cover.

The track may further comprise a fourth region, wherein the protrusion travels from the third region to the fourth region as the needle cover guide is rotated, wherein proximal movement of the needle cover from the locked position to the retracted position is allowed when the protrusion is in the fourth region.

The medicament delivery device may further comprise an actuation member, wherein the actuation member is actuatable by a user to rotate the needle cover guide relative to the needle cover such that the protrusion travels from the third region to the fourth region.

At least one of the actuation member or the needle cover guide may comprise a ramped surface configured to convert linear movement of the actuation member into rotation of the needle cover guide.

The actuation member may comprise a button arranged at a proximal end of the medicament delivery device.

The latch may comprise an engaging element configured to: engage an engaging element of the component of the medicament delivery mechanism when the latch is in the engaged position; and be disengaged from the engaging element of the component when the latch is in the disengaged position.

The engaging element of the latch may comprise a projection and the engaging element of the component may comprise a recess.

The component of the medicament delivery mechanism may be a collar that is rotatable relative to the body to dispense the medicament, wherein the latch is configured to engage the collar when in the engaged position to limit rotation of the collar.

The latch may be biased from the engaged configuration to the disengaged configuration, wherein the latch is held in the engaged position by the needle cover when the needle cover is in the extended position, and wherein the needle cover comprises a recess configured to receive at least a portion of the latch when the needle cover is in the retracted position such that the latch can move to the disengaged position.

The medicament delivery device may further comprise a needle cover lock that is movable by the medicament delivery mechanism between an initial configuration, in which movement of the needle cover from the extended position to the retracted position is not limited by the needle cover lock, and a locking position, in which movement of the needle cover from the extended position to the retracted position is limited by the needle cover lock.

The needle cover lock may be moved from the disengaged position to the engaged position by a plunger of the medicament delivery mechanism.

The medicament delivery device may further comprise the medicament. The medicament may be held in a container of the medicament delivery device.

A second aspect of this disclosure provides a method of operating a medicament delivery device disclosed herein, the method comprising: moving a needle cover of the medicament delivery device from an extended position to a retracted position to initiate delivery of a medicament; moving the needle cover of the medicament delivery device from the retracted position to the extended position to pause the delivery of the medicament; and resuming the delivery of the medicament by: actuating an actuation member of the medicament delivery device to rotate a needle cover guide; and subsequent to actuating the actuation member, moving the needle cover from the extended position to the retracted position.

BRIEF DESCRIPTION OF THE FIGURES

Exemplary embodiments of the present disclosure are described with reference to the accompanying drawings, in which:

FIG. 1A shows an injector device with a cap attached;

FIG. 1B shows the injector device of FIG. 1A with the cap removed;

DETAILED DESCRIPTION

Figure 2:
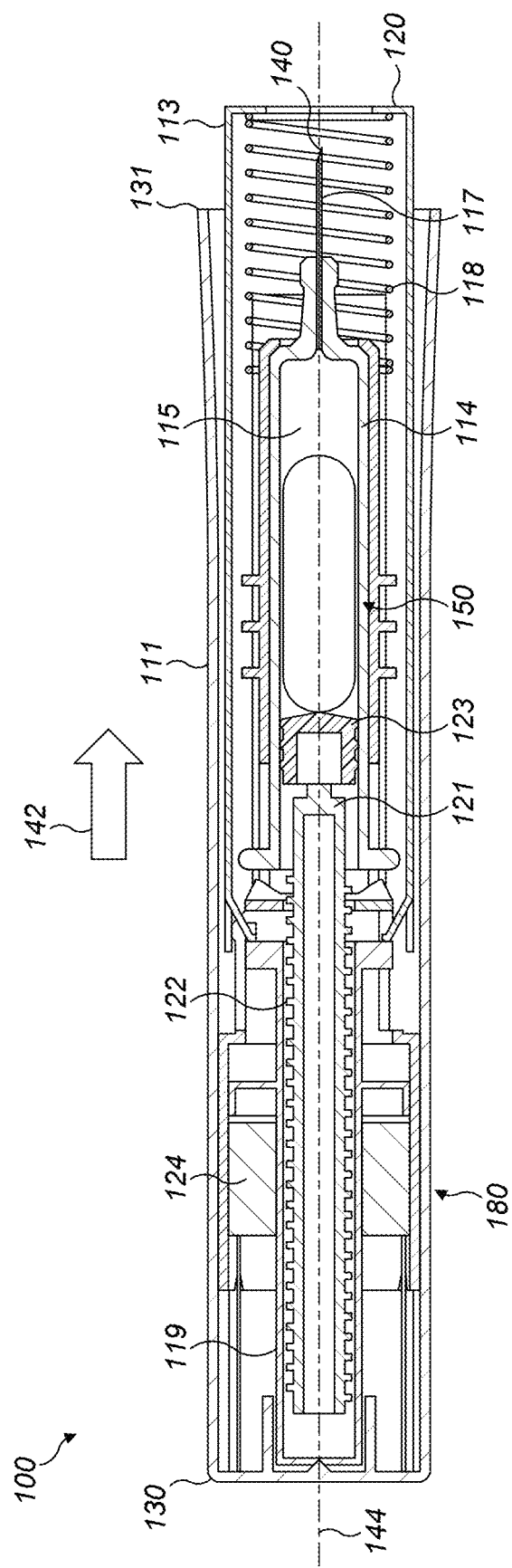
FIG. 2 is a cross-sectional view of a medicament delivery device.

Aspects of the present disclosure can allow a user to initiate, pause and/or resume the delivery of a medicament by a medicament delivery device.

A drug delivery device (also referred to as a medicament delivery device), as described herein, may be configured to inject a medicament into a subject (e.g., a patient). For example, delivery could be sub-cutaneous, intra-muscular, or intravenous. Such a device could be operated by the subject themselves (i.e., 'self-administration') or by a different user, such as a nurse or physician providing care to the subject, and can include various types of safety syringe, pen-injector, or auto-injector. The device can include a cartridge-based system that requires piercing a sealed ampule before use. Volumes of medicament delivered with these various devices can range from about 0.5 ml to about 2 ml (e.g., to about 2.25 ml). Yet another device can include a large volume device ("LVD") or patch pump (in some instances referred to as an on body injector (OBI) or on body device (OBD)), configured to adhere to a subject's skin for a period of time (e.g., about 5, 15, 30, 60, or 120 minutes) to deliver a "large" volume of medicament (typically about 2 ml to about 10 ml, or about 2 mL to about 20 mL).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve (also referred to as a needle cover), or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle sleeve in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament 15 into a subject's body. Device 10 includes a housing 11, which may also be referred to as a body, which typically contains a reservoir 14 containing the medicament 15 to be injected (e.g., a syringe) and the components required to facilitate one or more steps of the delivery process. Device 10 can also include a cap assembly 12 that can be detachably mounted to the housing 11. Typically, a user must remove cap 12 from housing 11 before device 10 can be operated. Device 10 can include a window 11a through which a user may view medicament 15 remaining in the reservoir 14.

As shown, housing 11 is substantially cylindrical and has a substantially constant diameter along the longitudinal axis X. The housing 11 has a distal region 20 and a proximal region 21. The term "distal" refers to a location that is relatively closer to a site of injection, and the term "proximal" refers to a location that is relatively further away from the injection site.

Device 10 can also include a needle sleeve 13 coupled to housing 11 to permit movement of the needle sleeve 13 relative to housing 11. For example, needle sleeve 13 can move in a longitudinal direction parallel to longitudinal axis X. Specifically, movement of needle sleeve 13 in a proximal direction can permit a needle 17 to extend from distal region 20 of housing 11.

Insertion of needle 17 can occur via several mechanisms. For example, needle 17 may be fixedly located relative to housing 11 and initially be located within an extended needle sleeve 13. Proximal movement of needle sleeve 13 by placing a distal end of sleeve 13 against a subject's body and moving housing 11 in a distal direction will uncover the distal end of the needle 17. Such relative movement allows the distal end of the needle 17 to extend into the injection site, such as a portion of the subject's body. Such insertion is termed "manual" insertion as needle 17 is manually inserted via the subject's manual movement of housing 11 relative to the needle sleeve 13.

Another form of insertion is "automated," whereby the needle 17 moves relative to housing 11. Such insertion can be triggered by movement of the needle sleeve 13 or by another form of activation, such as, for example, a button 22. As shown in FIGS. 1A & 1B, the button 22 is located at a proximal end of housing 11. However, in other embodiments, the button 22 could be located on a side of housing 11.

Other manual or automated features can include drug injection or needle retraction, or both. Injection is the process by which a bung or piston 23 is moved from a proximal location within a syringe (not shown in FIGS. 1A and 1B) to a more distal location within the syringe in order to force a medicament 15 from the syringe through needle 17. In some embodiments, a biasing member such as a drive spring (not shown in FIGS. 1A and 1B) is under compression before device 10 is activated. A proximal end of the drive spring can be fixed within proximal region 21 of housing 11, and a distal end of the drive spring can be configured to apply a compressive force to a proximal surface of piston 23. Following activation, at least part of the energy stored in the drive spring can be applied to the proximal surface of piston 23. This compressive force can act on piston 23 to move it in a distal direction. Such distal movement acts to compress the liquid medicament 15 within the syringe, forcing it out of needle 17.

Following injection, needle 17 can be retracted within the needle sleeve 13 or housing 11. Retraction can occur when the needle sleeve 13 moves distally as a user removes device 10 from a subject's body. This can occur as needle 17 remains fixedly located relative to housing 11. Once a distal end of sleeve 13 has moved past a distal end of needle 17, and needle 17 is covered, sleeve 13 can be locked. Such locking can include locking any proximal movement of sleeve 13 relative to housing 11.

Another form of needle retraction can occur if needle 17 is moved relative to housing 11. Such movement can occur if the syringe within housing 11 is moved in a proximal direction relative to housing 11. This proximal movement can be achieved by using a retraction spring (not shown), located in distal region 20. A compressed retraction spring, when activated, can supply sufficient force to the syringe to move it in a proximal direction. Following sufficient retraction, any relative movement between needle 17 and housing 11 can be locked with a locking mechanism. In addition, button 22 or other components of device 10 can be locked as required.

FIG. 2 shows a simplified view of a medicament delivery device 100 that extends along an axis 144. The medicament delivery device 100 may share one or more features with the drug delivery device 10 discussed in relation to FIGS. 1A and 1B.

The medicament delivery device 100 may be configured to inject greater than 2 ml of medicament and/or the medicament delivery device 100 may be configured to inject medicament having a viscosity of greater than 25 cP. Nevertheless, in other examples the medicament delivery device 100 may be configured to inject 2 ml or less of medicament and/or the medicament delivery device 100 may be configured to inject medicament having a viscosity of 25 cP or less.

The medicament delivery device 100 has a body 111 having a proximal end 130 and a distal end 131 arranged along the axis 144, a hollow needle 117 for injecting medicament 115, and a needle cover 113. The body 111 is shown to be substantially cylindrical, however it should be understood that the body 111 may have a different shape in other examples.

The body 111 houses a pre-filled syringe 150, which comprises a container 114 containing the medicament 115. The needle 117 is coupled to a distal end of the container 114 and is in fluid communication with an interior of the container 114 such that the medicament 115 may be dispensed from the container 114, via the needle 117. FIG. 2 shows the needle 117 permanently coupled to the container 114, however it should be understood that this is not meant to be limiting. For example, in other instances, the needle 117 may be removably couplable to the container 114 (e.g., via a Luer lock interface between a connector on the container 114 and a connector coupled to the needle 117) such that the needle 117 may be coupled to the container 114 prior to an injection and uncoupled from the container 114 after an injection (e.g., to replace the needle 117 with a new needle 117).

The syringe 150 further comprises a bung or piston 123 arranged within the container 114, proximal to the medicament 115 and the needle 117. The piston 123 is arranged within the container 114 to be moved distally to force the medicament 115 out of the container 114, via the needle 117.

The needle 117 has a distal end 140. The needle cover 113 is proximally movable relative to the body 111 between an extended position, in which the needle cover 113 covers the distal end 140 of the needle 117, and a retracted position, in which the distal end 140 of the needle 117 protrudes from the needle cover 113 for penetration into an injection site. FIG. 2 shows the device 100 with the needle cover 113 in the extended position. The medicament delivery device 100 further comprises a needle cover biasing member 118, such as a spring, configured to bias the needle cover 113 axially in the distal direction. The distal direction is indicated by the direction of the arrow 142 in FIG. 2.

The medicament delivery device 100 comprises a medicament delivery mechanism 180 for dispensing the medicament 115 from the syringe 150 held within the body 111. The medicament delivery mechanism 180 comprises a plunger 121, a collar 119 and a drive member 124.

The plunger 121, which may be coaxial with the axis 144, is axially movable within the syringe 150 of the device 100 in a distal direction to dispense the medicament 115 from the syringe 150 via the needle 117. The plunger 121 is arranged to engage the piston 123 of the syringe 150 such that distal axial movement of the plunger 121 moves the piston 123 distally to dispense the medicament 115 via the needle 117.

The collar 119, which may also be coaxial with the axis 144, is axially fixed relative to the body 111 but is rotatable within the body 111 (e.g., about the axis 144). The drive member 124 is configured to rotate the collar 119 when the drive member 124 is actuated/released. For example, the drive member 124 may be a spring (e.g., a torsion spring), wherein the spring is configured to rotate the collar 119 when the spring is released. However, it should be understood that one or more other types of drive member 124 may be used instead, such as a pneumatic drive member. The drive member 124 is released when the needle cover 113 reaches a predetermined axial displacement with respect to the body 111.

The collar 119 and the plunger 121 are arranged such that the rotation of the collar 119 by the drive member 124 causes the plunger 121 to move distally within the syringe 150, to thereby dispense the medicament 115 from the syringe 150 via the needle 117. For example, the plunger 121 may comprise an external screw thread 122 that is configured to interface with an internal screw thread of the collar 119 such that rotation of the collar 119 causes distal translation of the plunger 121. However, it should be understood that other forms of interface between the collar 119 and the plunger 121 for converting rotation of the collar 119 into translation of the plunger 121 may be used instead. For example, in other instances, only one of the collar 119 and the plunger 121 may have a screw thread, and the other of the collar 119 and the plunger 121 may have one or more engagement features, such as one or more projections, that are arranged to engage with the screw thread such that rotation of the collar 119 causes translation of the plunger 121.

To initiate delivery of the medicament 115 into a subject (who may be the user of the medicament delivery device 100, a different person to the user of the device, or an non-human animal), a distal end 120 of the needle cover 113 is to be pressed against the injection site on the subject and the body 111 is moved towards the injection site, thereby moving the needle cover 113 axially into the body 111 and uncovering the needle 117 from within the needle cover 113 such that it penetrates the injection site. The proximal axial displacement of the needle cover 113 causes the release of the drive member 124, which rotates the collar 119. The rotation of the collar 119 moves the plunger 121 axially within the syringe 150 to dispense the medicament 115 into the injection site via the needle 117. The device 100 is pressed against the injection site to hold the needle cover 113 in its retracted position whilst the medicament 115 is dispensed from the device 100.

After the medicament 115 has been dispensed, the device 100 is removed from the injection site by moving the body 111 away from the injection site. In doing so, the needle cover 113 moves distally under the force of the biasing member 118 towards the extended position to cover the distal end 140 of the needle 117 and therefore protect the user and/or subject from an accidental needle-stick event. In some instances, subsequent proximal movement of the needle cover 113 relative to the body 111 may be inhibited by a locking mechanism.

FIGS. 3A to 3F show a simplified cross-section view of a medicament delivery device 200 in various stages of operation, in accordance with one or more aspects of the present disclosure.

The features described and/or contemplated in relation to the medicament delivery device 200 may be incorporated in the medicament delivery device 100 described and/or contemplated above in relation to FIG. 2. Alternatively or additionally, the features described and/or contemplated in relation to the medicament delivery device 200 may be incorporated in another medicament delivery device, for example a medicament delivery device having a different mechanism for dispensing a medicament to that described in relation to the medicament delivery device 100. Like references refer to like features.

Figure 3A:
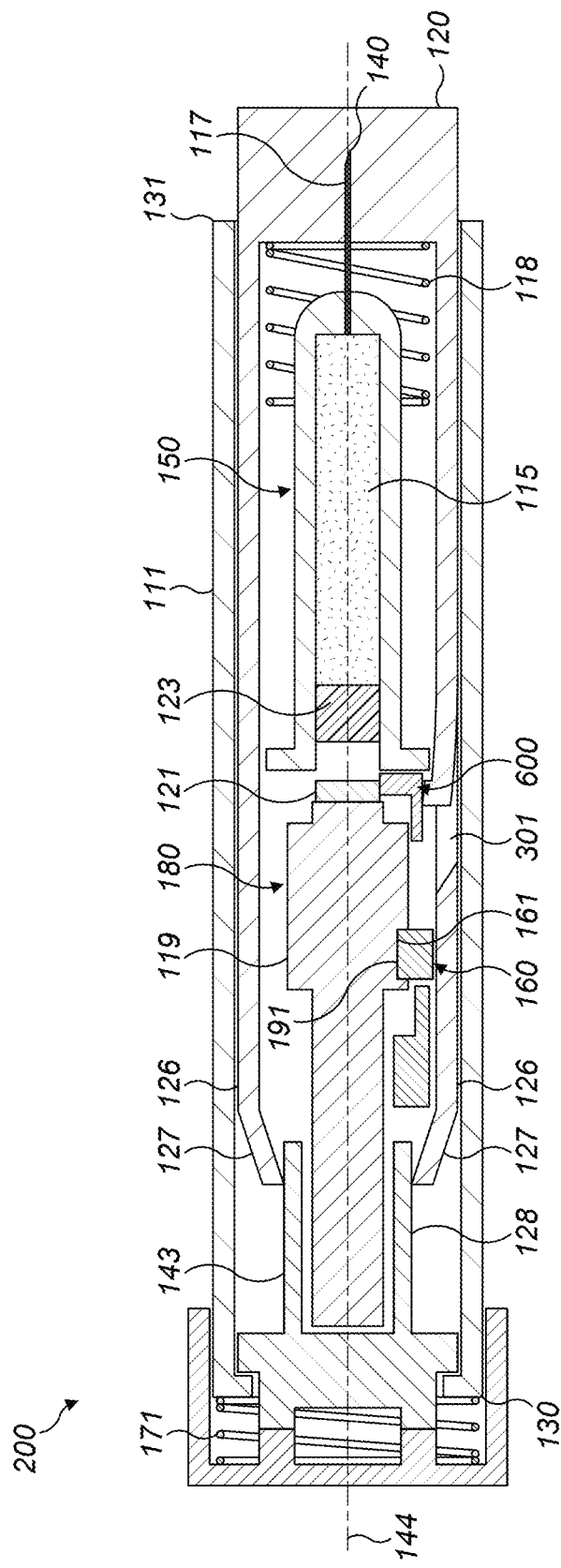
FIG. 3A is a schematic cross-sectional view of a medicament delivery device in accordance with one or more embodiments, in an initial state.

With reference to FIG. 3A, the medicament delivery device 200 includes a body 111 extending along an axis 144 of the medicament delivery device 200 and having a proximal end 130 and a distal end 131. A syringe 150 containing a medicament 115 is held within the body 111.

The medicament delivery device 200 further includes a needle 117 for injecting the medicament 115 and a needle cover 113 axially movable relative to the body 111 between an extended position and a retracted position. When in the extended position, the needle cover 113 extends from the distal end 131 of the body 111 such that a distal end 140 of the needle 117 is surrounded, to protect a user from an accidental needle-stick injury prior to an actual injection. When the needle cover 113 is in the retracted position, the distal end 140 of the needle 117 protrudes distally from the distal end 120 of the needle cover 113 such that the distal end 140 of the needle 117 can penetrate an injection site. A needle cover biasing member 118, which in this example takes the form of a spring, is configured to bias the needle cover 113 distally, from the retracted position to the extended position. It should be understood that, in other examples, the needle cover biasing member 118 may take a different form to a spring, for example a pneumatic mechanism or an elastic polymer.

In FIG. 3A, the medicament delivery device 200 is shown in an initial state prior to an injection, in which the medicament delivery device 200 is not being held against an injection site. The needle cover 113 is in the extended position with respect to the body 111, biased into the extended position by the needle cover biasing member 118. The needle cover 113 is axially movable relative to the body 111 between the extended position shown in FIG. 3A, in which a distal end 120 of the needle cover 113 is distal to a distal end 140 of the needle 117, and the retracted position shown in FIG. 3B, in which the distal end 140 of the needle 117 is distal to the distal end 120 of the needle cover 113.

The medicament delivery device 200 comprises a medicament delivery mechanism 180 for dispensing the medicament 115 from the syringe 150 held within the body 111. The medicament delivery mechanism 180 in this example comprises a plunger 121, a collar 119 and a drive member such as a spring (e.g., torsion spring), one or more of which may be as described above in relation to the device 100. However, it should be understood that in other examples, the medicament delivery mechanism 180 may comprise one or more different components than a plunger 121, a collar 119 and/or drive member 124 described above in relation to the device 100.

The plunger 121, which may be coaxial with the axis 144, is axially movable within the syringe 150 of the medicament delivery device to dispense medicament 115 from the syringe 150 via the needle 117. The plunger 121 is located proximal to the piston 123 of the syringe 150. FIG. 3A shows that the distal end of the plunger 121 is initially axially separated from the piston 123 when the medicament delivery device 200 is in its initial state. However, it should be understood that in other examples the distal end of the plunger 121 may be engaged with the piston 123 when the medicament delivery device 200 is in its initial state.

The collar 119, which may be coaxial with the axis 144, is axially fixed relative to the body 111 but is able to rotate with respect to the body 111 (e.g., about the axis 144). The drive member (which is not shown in FIGS. 3A-3F to improve the clarity of the drawings, but which may be similar or identical in location and/or type to the drive member 124 previously described in relation to FIG. 2) is configured to rotate the collar 119 when released. The drive member may be a spring such as a torsion spring, however other forms of spring/drive member may be used instead.

The drive member (e.g., spring) is released when the needle cover 113 reaches a predetermined axial displacement relative to the body 111. The collar 119 interfaces with the plunger 121 (e.g. via any interface(s) previously described in relation to FIG. 2) such that the rotation of the collar 119 by the drive member causes the plunger 121 to move distally within the syringe 150 to thereby dispense medicament 115 from the syringe 150 via the needle 117 (e.g., in the same or similar manner as previously described in relation to FIG. 2).

The medicament delivery device 200 has a latch 160 that is releasably engageable with the medicament delivery mechanism 180 for initiating, pausing and resuming dispensing of the medicament 115 by the medicament delivery mechanism 180. The latch 160 is movable by the needle cover 113 between an engaged configuration, in which the latch 160 is engaged with a component of the medicament delivery mechanism 180 to prevent delivery of the medicament 115, and a disengaged configuration, in which the latch 160 is disengaged from the component of the medicament delivery mechanism 180 to allow (e.g. initiate and/or resume) delivery of the medicament 115. The latch 160 comprises an engaging element 161 configured to engage the component of the medicament delivery mechanism 180 when in the engaged configuration and to disengage the component of the medicament delivery mechanism 180 when in the disengaged configuration.

FIG. 3A shows the latch 160 in the engaged configuration. In this example, the component of the medicament delivery mechanism 180 that is engaged and disengaged by the latch 160 is the collar 119, as later described in more detail in relation to FIGS. 4A-4C. However, it should be understood that, in other examples, the latch 160 may be configured to engage a different component than the collar 119 to initiate, pause and/or resume medicament delivery. For example, the latch 160 may additionally/alternatively be configured to engage and disengage the plunger 121 and/or drive member to initiate, pause and/or resume medicament delivery.

Figure 4C:
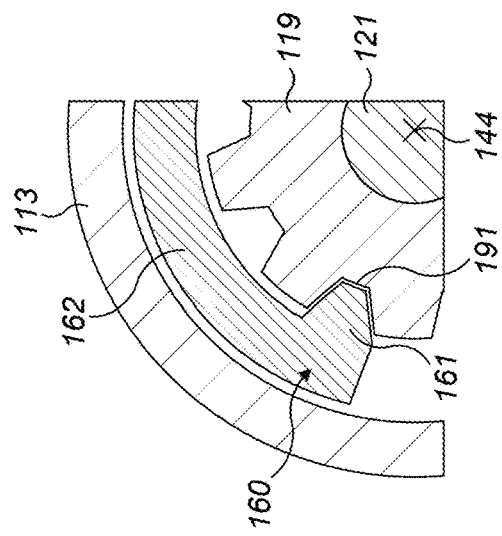
FIG. 4C is a schematic cross-sectional view of a portion of the medicament delivery device of FIG. 3C, showing the latch in the engaged configuration with the collar.
Figure 4B:
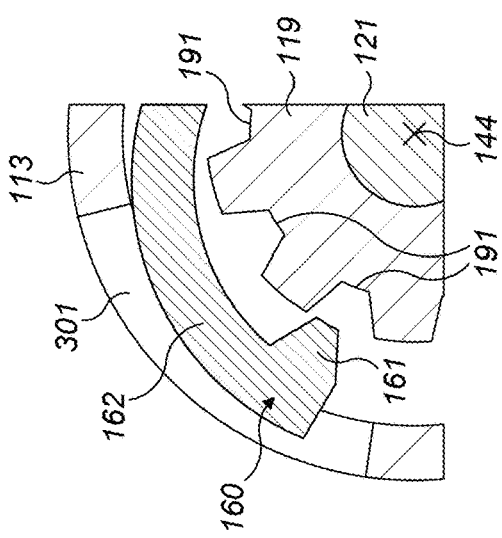
FIG. 4B is a schematic cross-sectional view of a portion of the medicament delivery device of FIG. 3B, showing the latch in a disengaged configuration with the collar.
Figure 4A:
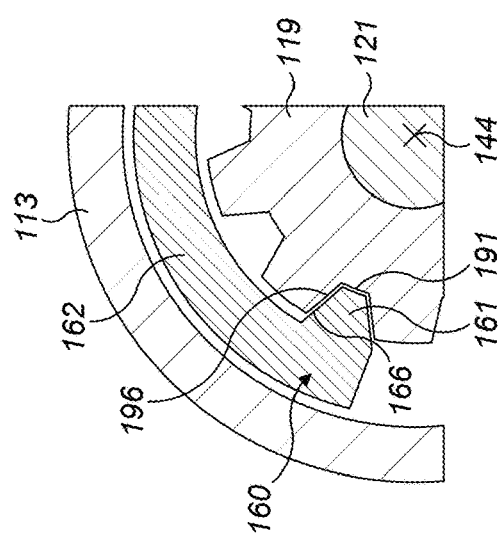
FIG. 4A is a schematic cross-sectional view of a portion of the medicament delivery device of FIG. 3A, showing a latch in an engaged configuration with a collar.

FIGS. 4A-4C each show a schematic cross-section of a portion of the medicament delivery device 200 to demonstrate operation of the latch 160, wherein the cross-section is in a plane that is normal to the axis 144.

FIG. 4A shows a cross-section through portions of the needle cover 113, latch 160, collar 119 and plunger 121 of the medicament delivery device 200 of FIG. 3A when the medicament delivery device 200 is in its initial state, with the latch 160 in its engaged configuration. The view in FIG. 4A is along the axis 144 of the medicament delivery device 200 (i.e., the axis 144 is normal to the page). The plunger 121 is arranged along the axis 144. The collar 119 is arranged radial to the plunger 121, such that it surrounds at least a portion of the plunger 121. The needle cover 113 is arranged radial to the collar 119 and plunger 121, such that it surrounds at least a portion of the collar 119 and plunger 121. The plunger 121, collar 119 and needle cover 113 may be concentric about the axis 144.

The collar 119 is biased to rotate about the axis 144 by the drive member for causing distal translation of the plunger 121, however rotation of the collar 119 is limited (e.g., prevented) while the medicament delivery device 200 is in the initial state by engagement of the latch 160 with the collar 119. The latch 160 comprises a flexible arm 162 that extends at least partially around the collar 119, between an outer surface of the collar 119 and an inner surface the needle cover 113. An engaging element 161, for example in the form of a protrusion, extends radially inwards from a free end of the flexible arm 162 to releasably engage with a corresponding engaging element 191 of the collar 119, in this example the engaging element 191 of the collar 119 being a recess on the outer surface of the collar 119. FIG. 4A shows the engaging element 161 of the latch 160 engaged with the engaging element 191 of the collar 119 such that rotation of the collar 119 relative to the latch 160 is limited. The latch 160 may be coupled to the body 111 such that engagement between the engaging element 161 of the latch 160 and the engaging element 191 of the collar 119 limits (e.g., prevents) rotation of the collar 119 relative to the body 111. As such, the medicament delivery mechanism 180 is inhibited from dispensing medicament 115 when engaged by the latch 160.

The latch 160 may be biased from the engaged configuration to the disengaged configuration. In FIG. 4A, the latch 160 is biased from the engaged configuration towards the disengaged configuration at least in part by the medicament delivery mechanism 180. More specifically, the collar 119 is biased to rotate by the drive member of the medicament delivery mechanism 180, wherein this biased rotation biases the engaging element 161 of the latch 160 out of engagement with the engaging element 191 of the collar 190, for example due to engagement between a side wall 166 of the engaging element 161 of the latch 160 and a side wall 196 of the engaging element 191 of the collar 119. In some examples, one or both of the side walls 166, 196 may be ramped (e.g., bevelled) to assist with biasing the engaging element 161 of the latch 160 to disengage the engaging element 191 of the collar 119. Additionally or alternatively, in some examples the latch 160 may be biased from the engaged configuration to the disengaged configuration at least in part by a resilient portion of the latch 160. For example, at least a portion of the flexible arm 162 may be formed of a resilient material that causes the free end of the flexible arm 162 to be biased radially outwards, to disengage the engaging element 161 of the latch 160 from the engaging element 191 of the collar 119. Other suitable mechanisms for biasing the latch 160 towards its disengaged configuration may be envisaged.

As shown in FIG. 4A, the latch 160 is held in the engaged configuration by an inner surface of the needle cover 113 when the needle cover 113 is in the extended position. As such, the free end of the flexible arm 162 is inhibited from moving radially away from the collar 119 and so the engaging element 161 (e.g. protrusion) of the latch 160 is held in engagement with the engaging element 191 of the collar 119 to limit rotation of the collar 119 while the needle cover 113 is in the extended position.

The needle cover 113 is configured such that proximal movement of the needle cover 113 from the extended position towards the retracted position moves the latch 160 from the engaged configuration to the disengaged configuration, as later described in relation to FIGS. 3B and 4B, while distal movement of the needle cover 113 from the retracted position towards the extended position moves the latch 160 from the disengaged configuration to the engaged configuration, as later described in relation to FIGS. 3C and 4C.

FIG. 4A shows the collar 119 may have a plurality of engaging elements 191 (e.g., recesses) arranged circumferentially around an outer surface of the collar 119 such that the engaging element 161 of the latch 160 remains aligned with one of those plurality of engaging elements 191 for engagement, regardless of the rotational position of the collar 119.

As shown in FIG. 3A, the medicament delivery device 200 further comprises a needle cover lock 600 for limiting proximal movement of the needle cover 113 after the completion of medicament delivery. FIG. 3A shows the needle cover lock 600 in an initial configuration, in which movement of the needle cover 113 from the extended position to the retracted position is not limited by the needle cover lock 600, therefore the needle cover 113 is free to move proximally. The needle cover lock 600 may be movable by the medicament delivery mechanism 180 between the initial configuration and a locking configuration, wherein movement of the needle cover 113 from the extended position to the retracted position is limited by the needle cover lock 600 when in the locking configuration. In some examples, the needle cover lock 600 may be moved from the disengaged position to the engaged position by distal movement of the plunger 121 of the medicament delivery mechanism 180. Operation of the needle cover lock 600 is described in more detail later, in relation to FIGS. 6A-6D.

As shown in FIG. 3A, the needle cover 113 of the medicament delivery device 200 comprises a pair of arms 126. The arms 126 extend in a proximal direction from the remainder of the needle cover 113. It should be understood that in other examples the needle cover 113 may comprise a different number of arms 126 to two, for example the needle cover 113 may comprise a single arm 126 or more than two arms 126 (e.g., three arms 126 or four arms 126 etc.).

The or each arm 126 has a protrusion 127. The protrusion 127 is at the free (e.g., proximal) end of the or each arm 126, although in other embodiments the protrusion 127 may be located distally from the free end of the arm(s) 126. The arm(s) 126 and/or protrusion(s) 127 may be flexible, as discussed later.

FIG. 3A shows the pair of arms 126 and respective protrusions 127 arranged symmetrically about the axis 144 (e.g., with a rotational symmetry of 180 degrees about the axis 144). However, it should be understood that this is not meant to be limiting and that other arrangements are possible. For example, the pair of arms 126 may be separated by an angle of 90 degrees about the axis 144.

The medicament delivery device 200 has a needle cover guide 143, which may be arranged at least partially within the body 111. The needle cover guide 143 comprises a track 128 arranged on its outer circumferential surface. In some examples a separate track 128 is provided for each arm 126 (if more than one arm 126 is present), or a single track 128 may be used for each arm 126.

The medicament delivery device 200 further comprises an actuation member 170 configured to engage the needle cover guide 143, as described later in relation to FIGS. 5A-5E. FIG. 3A shows the actuation member 170 taking the form of a button arranged at a proximal end of the medicament delivery device 200. However, it should be understood that the actuation member 170 may, in other examples, take a different form to a button, and/or be located at a different location of the medicament delivery device 200 and/or body 111.

The actuation member 170 is actuatable by a user between a first position and a second position relative to the body 111. FIG. 3A shows the actuation member 170 in the first position relative to the body 111, while FIG. 3D shows the actuation member 170 in the second position relative to the body 111, the actuation member 170 having been moved distally relative to the body 111 from the first position to the second position by actuation (e.g., movement in the distal direction) of the actuation member 170 by a user. A user may directly press the actuation member 170 to move it distally between the first position and the second position, for example by pushing a proximally-facing surface of the actuation member 170 distally with a finger or thumb. The actuation member 170 may be biased from its second position to its first position by an actuation member biasing member such as a spring 171, however other forms of actuation member biasing member to a spring 171 may be envisaged.

The or each arm 126 engages the track 128 of the needle cover guide 143 via the protrusion(s) 127. The track 128 is configured to limit a proximal movement of the needle cover 113 relative to the body 111, after the needle cover 113 has moved from the retracted position back to the extended position. That is, the or each arm 126 is configured to engage the track 128 such that a proximal movement of the needle cover 113 is limited after the needle cover 113 has moved from the retracted position to the extended position.

The needle cover guide 143 is substantially cylindrical and is rotatable relative to the body 111, for example about the axis 144, but is axially fixed relative to the body 111. FIG. 3A shows the needle cover guide 143 arranged at a proximal end of the medicament delivery device 200, however it should be understood that in other examples the needle cover guide 143 may be located at a different location of the medicament delivery device 200, for example distal to the proximal end of the medicament delivery device 200.

The needle cover guide 143, track 128 and actuation member 170 are shown in greater detail in FIGS. 5A-5E.

FIGS. 5A-5E show the needle cover guide 143, track 128 and actuation member 170 of the medicament delivery device 200 of FIGS. 3A-3F in various operational states. In each of FIGS. 5A-5E, only a portion of (e.g., a proximal end of) the arms 126 is shown. Portions of the actuation member 170 are shown as see-through, so that interaction between the actuation member 170 and the needle cover guide 143 is visible. Various other features of the medicament delivery device 200 such as the spring 171 and body 111 are hidden in FIGS. 5A-5E, for clarity.

Figure 5A:
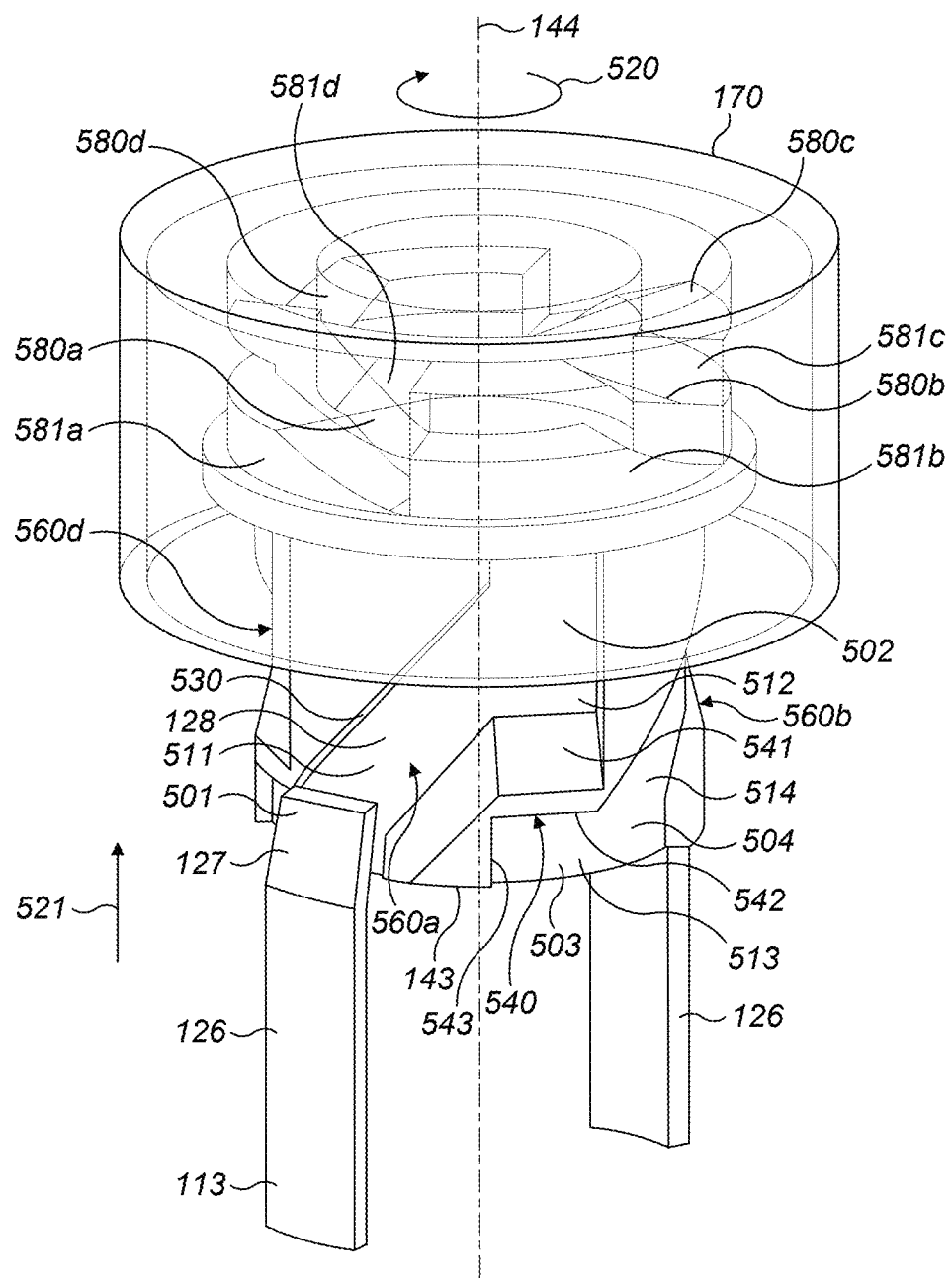
FIG. 5A is a partial perspective view of the needle cover guide, needle cover and actuation member of the medicament delivery device of FIG. 3A.

FIG. 5A shows the needle cover guide 143, needle cover 113 and actuation member 170 in a first configuration, corresponding to their configuration in FIG. 3A. As shown in FIG. 5A, the track 128 extends at least partially around a circumference of the needle cover guide 143 for rotating the needle cover guide 143 as the needle cover 113 moves from the extended position to the retracted position.

As shown in FIG. 5A, the arms 126 are positioned radially outwardly of the needle cover guide 143, with the protrusion 127 extending radially inwards to engage the track 128 arranged at the outer circumferential surface of the needle cover guide 143. However, it should be understood that in one or more other embodiments, the arms 126 are instead positioned radially inwardly of the needle cover guide 143, with the protrusions 127 extending radially outwards to engage the track 128 arranged at an inner circumferential surface of the needle cover guide 143.

The track 128 comprises a first region 511, a second region 512, a third region 513 and a fourth region 514. When the medicament delivery device 200 is in its initial state shown in FIG. 3A, with the needle cover 113 in the extended position, the or each arm 126 engages the track 128 via its protrusion 127 at a respective first position 501 within the first region 511 (see FIG. 5A). The first position 501 may be located near a distal end of the needle cover guide 143, at a distal end of the first region 511.

As shown in FIG. 5A, the first region 511 extends at least partially around the circumference of the needle cover guide 143. The first region 511 and the second region 512 are arranged such that the protrusion 127 travels from the first position 501 within the first region 511 to a second position 502 within the second region 512 as the needle cover 113 moves (e.g., as indicated by arrow 521) from the extended position to the retracted position (as later described in relation to FIG. 5B). The first region 511 has an axially-extending component of direction and is at an acute angle relative to the axis 144 of the medicament delivery device 200, extending helically about the outer surface of the needle cover guide 143. The needle cover guide 143 therefore rotates (e.g., as indicated by arrow 520) when the protrusion 127 travels along the first region 132 of the track 128, due to engagement between the protrusion 127 and an angled proximal side wall 530 of the first region 501.

The second region 512 of the track 128 extends axially along the needle cover guide 143 such that the protrusion 127 travels distally within the second region 512 as the needle cover 113 moves distally, from its retracted position to its extended position, without causing the needle cover guide 143 to be rotated.

The third region 513 is located distal to the second region 512 but axially aligned with the second region 512, such that the protrusion 127 travels distally from the second position 502 in the second region 512 to a third position 503 in the third region 513 as the needle cover 113 moves distally from the retracted position to the extended position, as described later.

The track 128 comprises a locking element 540 arranged at a distal end of the second region 512, proximal of the third region 513. The locking element 540 is configured to limit proximal movement of the needle cover 113 after the needle cover 113 has moved from the retracted position to the extended position (and therefore after the protrusion 127 has moved from the second position 502 to the third position 503). The locking element 540 comprises a proximally-facing ramped surface 541 and a distally-facing locking surface 542 which may be substantially perpendicular to the axis 144. Operation of the locking element 540 shall be described later.

The third region 513 may have a side wall 543 to limit back-rotation (e.g., rotation in a direction opposite to the rotation indicated by arrow 520) of the needle cover guide 143 once the protrusion 127 is in the third position 503.

The third region 513 and the fourth region 514 extend circumferentially around the needle cover guide 143 and are arranged adjacent to each other such that, when the protrusion 127 is in the third position 503 of the third region 513 and the needle cover guide 143 is rotated relative to the needle cover 113 in the direction indicated by the arrow 520, the protrusion travels from the third position 503 in the third region 513 to a fourth position 504 in the fourth region 514.

The fourth region 514 may be substantially the same as the first region 511 (e.g., same features etc.), but located at a different circumferential position about the outer circumferential surface of the needle cover guide 143. That is, the track 128 may comprise a plurality of portions 560 arranged circumferentially around the needle cover guide 143, each portion 560 comprising a respective first region 511, second region 512 and third region 513, wherein each first region 511, second region 512 and third region 513 may be substantially similar or identical. Each first region 511, second region 512 and third region 513 of each portion 560 may be spaced about the circumferential outer surface of the needle cover guide 154 such that a first position 501 and first region 511 of one portion 560 acts as the fourth position 504 and fourth region 514 of an adjacent portion 560 of the track 128. The plurality of portions 560 may be repeated around the entire outer circumferential surface of the needle cover guide 143 such that all of the portions 560 are linked, allowing the protrusion 127 to travel through the first to fourth regions 511, 512, 513, 514 of each portion 560 in order, in a continuous loop around the needle cover guide 143.

FIGS. 5A-5D show the track 128 comprising four identical portions 560a, 560b, 560c, 560d arranged circumferentially around the needle cover guide 143, each portion 560a, 560b, 560c, 560d comprising a respective first region 511, second region 512 and third region 513. The four portions 560a, 560b, 560, 560d are spaced 90 degrees apart around the circumference of the needle cover guide 143, such that the needle cover guide 143 has a rotational symmetry of four about the axis 144. While one of the arms 126 engages with a first portion 560a of the track, the other of the arms 126 simultaneously engages with a different portion of the track 128 (e.g., the third portion 560c) such that movements of a protrusion 127 in the first portion 560a of the track 128 mirror movements of the other protrusion 127 in the other portion (e.g., the third portion 560c) of the track 128.

It should be understood that in other examples, there may be a different number of identical portions 560a-d of the track 128 to four located around the needle cover guide 143. For example, there may be two identical portions 560, three identical portions 560, or five or more identical portions 560, each portion 560 having first to fourth regions 511, 512, 513, 514. In other examples, only a single portion 560 may be present, with the portion 560 extending around the entire circumference of the needle cover guide 143 such that the first position 501 and first region 511 of the portion 560 also act as the fourth position 504 and fourth region 514.

FIG. 5A also shows the actuation member 170, which has four ramped engagement elements 580a-580d extending distally from a distal-facing inner surface of the actuation member 170. Each engagement element 580a-580d is configured to engage a respective one of four corresponding ramped engagement elements 581a-581d of the needle cover guide 143, the engagement elements 581a-581d extending proximally from a proximal-facing surface of the needle cover guide 143. The four engagement elements 580a-580d of the actuation member are arranged in a circular pattern about the axis 144, as are the four corresponding engagement elements 581-581d of the needle cover guide 143. FIG. 5A shows the actuation member 170 biased in its first position.

The four engagement elements 580a-580d of the actuation member and the four corresponding engagement elements 581-581d of the needle cover guide 143 are currently arranged such that a distal actuation of the actuation member 170 towards the needle cover guide 143, from its first position to its second position, does not cause the needle cover guide 143 to substantially rotate. Each of the four engagement elements 580a-580d has a corresponding distally-facing ramped surface 582a-582d, while each of the four engagement elements 581-581d has a corresponding proximally-facing ramped surface 583a-583d. The distally-facing ramped surfaces 582a-582d are configured to engage the proximally-facing ramped surfaces 583a-583d, as described later.

While FIG. 5A shows four engagement elements 580a-580d and four corresponding engagement elements 581-581d, it should be noted that in other cases fewer or more than four engagement elements 580a-580d and/or engagement elements 581-581d may be present.

Figure 3B:
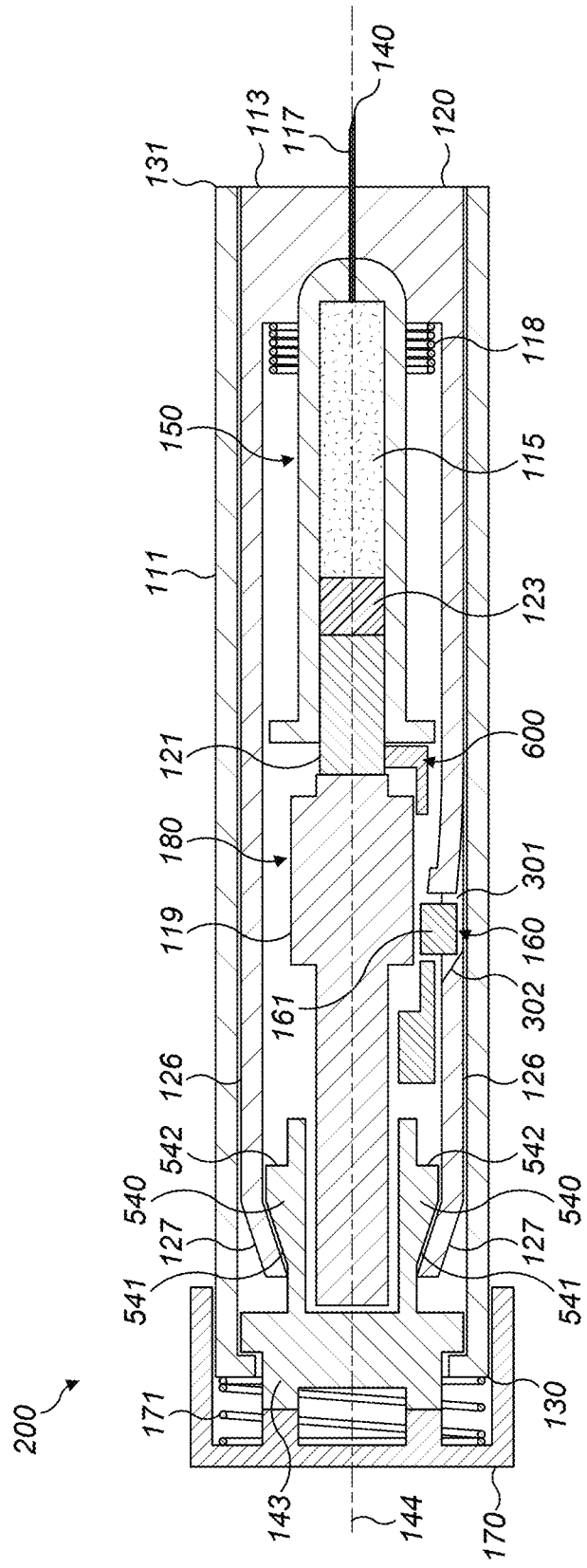
FIG. 3B is a schematic cross-sectional view of the medicament delivery device of FIG. 3A, in an holding state.

FIG. 3B shows the medicament delivery device 200 of FIG. 3A in a holding state, in which the needle cover 113 has been moved axially in a proximal direction with respect to the body 111. The needle cover 113 is shown in its retracted position, in which the distal end 140 of the needle 117 extends distal to the distal end 120 of the needle cover 113. The user has placed the distal end 120 of the needle cover 113 against an injection site and moved the body 111 towards the injection site, causing the needle cover 113 to move proximally towards its retracted position (shown in FIG. 3B) and allowing the distal end 140 of the needle 117 to penetrate an injection site of the subject (wherein the subject may be the user, or a different person to the user).

As the needle cover 113 is moved proximally, the latch 160 is moved from its engaged configuration to its disengaged configuration. As such, the latch 160 will be brought out of engagement with the component (e.g., collar 119) of the medicament delivery mechanism 180, thereby allowing the medicament 115 to be dispensed.

FIG. 3B shows that proximal movement of the needle cover 113 has brought a recess 301 in the needle cover 113 into alignment with the latch 160 such that the latch 160 moves from its engaged configuration to its disengaged configuration with respect to the collar 119.

FIG. 4B shows the latch 160 in its disengaged configuration, corresponding to FIG. 3B. The needle cover 113 has been moved proximally (e.g., parallel to the axis 144, out of the page) from the extended position to the retracted position, bringing the needle cover recess 301 into alignment with the flexible arm 162 of the latch 160. The flexible arm 162 is no longer held in its engaged position by the needle cover 113, therefore the flexible arm 162 can now flex radially outwards, into the needle cover recess 301, due to the biasing of the flexible arm 162 from its engaged configuration to its disengaged configuration. Radial movement of the flexible arm 162 outwards brings the engaging element 161 (e.g., projection) of the latch 160 out of engagement with the engaging element 191 (e.g., recess) of the collar 119 such that the latch 160 is now in its disengaged configuration and rotation of the collar 119 by the drive member is no longer limited by the latch 160.

Returning to FIG. 3B, it can be seen that disengagement of the latch 160 from the collar 119 has initiated medicament delivery. Disengagement of the latch 160 from the collar 119 has allowed the collar 119 to be rotated by the drive member and, through interaction between the collar 119 and the plunger 121, cause the plunger 121 to move axially in a distal direction to engage the piston 123 (if not already engaged) and move the piston 123 distally to dispense at least a portion of the medicament 115 into the injection site. The delivery of medicament 115 is not yet complete, therefore the needle cover lock 600 remains in its in its initial configuration in which proximal movement of the needle cover 113 is not limited by the needle cover lock 600.

It is also shown in FIG. 3B that proximal movement of the needle cover 113 from the extended position to the retracted position has rotated the needle cover guide 143, due to the engagement between the arms(s) 126 and the track 128. Proximal movement of the needle cover 113 and rotation of the needle cover guide 143 has moved the locking element(s) 540 of the needle cover guide 143 relative to the projection(s) 127 such that it is (they are) now distal to the projection(s) 127 and axially aligned relative to the projection(s) 127.

Figure 5B:
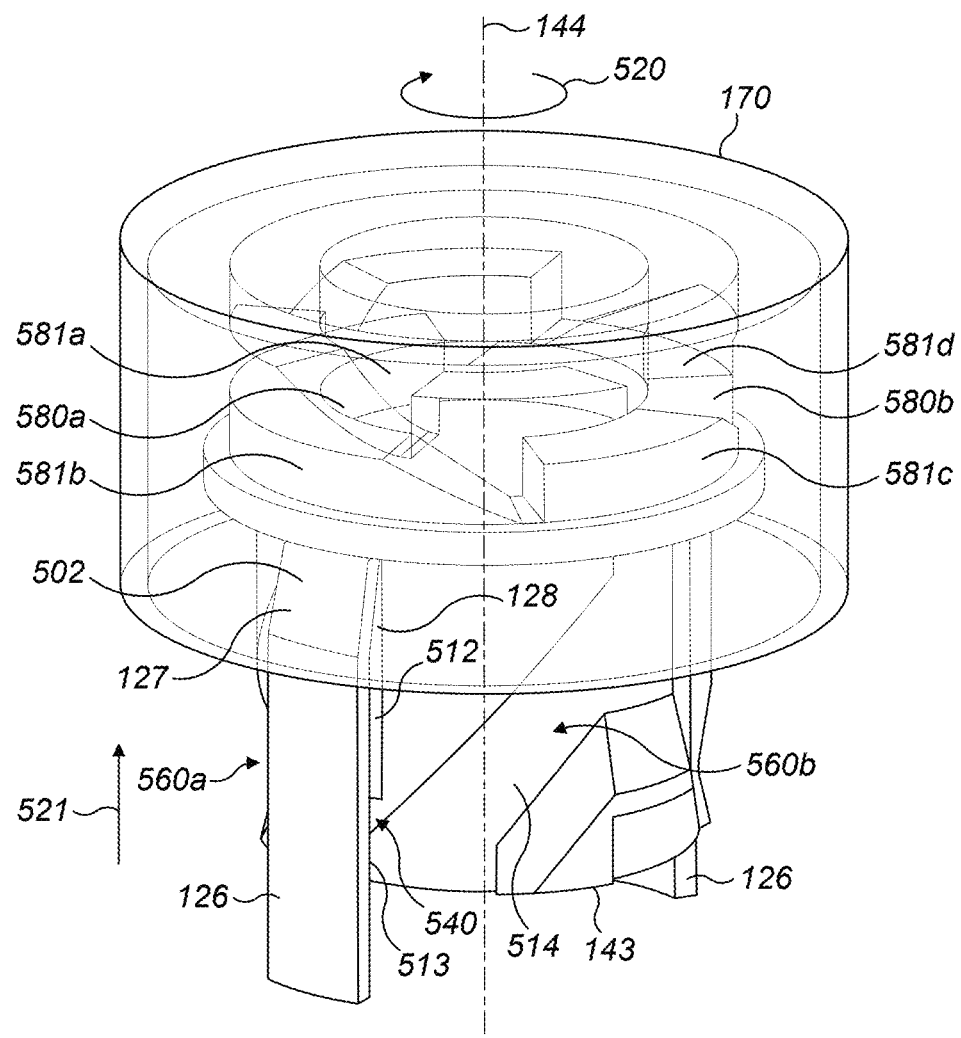
FIG. 5B is a partial perspective view of the needle cover guide, needle cover and actuation member of the medicament delivery device of FIG. 3B.

FIG. 5B shows the needle cover guide 143, needle cover 113 and actuation member 170 in a second configuration, corresponding to their configuration in FIG. 3B. As the needle cover 113 has moved axially from the extended position to the retracted position (i.e., 'upwards' between FIG. 5A and FIG. 5B, as indicated by arrow 521), the projection(s) 127 of the flexible arm(s) 126 has travelled from the first position 501, in the first region 511 of the track 128, to the second position 502, in the second region 512 of the track 128, causing the needle cover guide 143 to rotate (e.g., as indicated by the arrow 520) relative to the arm(s) 126. The second position 502 is at a proximal end of the second region 512, with the second position 502 proximal to the first position 501 and spaced from the first position 501 circumferentially around the circumferential outer surface of the needle cover guide 143.

FIG. 5B shows the actuation member 170 remains in its first position and has not rotated relative to the needle cover 113. However, the needle cover guide 143 has rotated relative to the actuation member 170 such that the engagement elements 581a-581d of the needle cover guide 143 have been rotated relative to the engagement elements 580a-580d of the actuation member 170, bringing them into a new alignment with the engagement elements 580a-580d. The engagement elements 581a-581d of the needle cover guide 143 and the engagement elements 580a-580d of the needle cover guide 143 are now in a relative configuration such that a distal movement of the actuation member 170 from its first position to its second position would cause the needle cover guide 143 to be rotated relative to the actuation member 170 and needle cover 113 in the direction indicated by arrow 520, as described later.

Once the medicament delivery process has been initiated, the drive member of the medicament delivery mechanism 180 will continue to automatically dispense the medicament 115. However, the user of the medicament delivery device 200 may wish to pause the medicament delivery process after it has been initiated, before the entire medicament 115 has been dispensed.

A user may wish to pause a medicament delivery process after only a portion of the medicament 115 has been delivered to a subject such that one or more remaining portions of the medicament 115 may be delivered to the same subject (or another subject) at a later time. The user may wish to deliver the medicament 115 in a plurality of doses because the subject is experiencing discomfort during the medicament delivery process, for example due to the volume of the medicament 115 being delivered and/or the rate at which the medicament 115 is being delivered. Additionally or alternatively, the user may wish to deliver the medicament 115 in a plurality of discrete doses spaced apart in time because the dosage regimen of the medicament 115 requires such a method of administration (e.g., the dosage regimen requires three doses to be delivered, each separated by one hour). Additionally or alternatively, the user may have inserted the needle 117 of the medicament delivery device 200 at an incorrect injection site and would like to pause the medicament delivery process so that the needle 117 may be removed and repositioned at a correct injection site. It should be understood that this list of reasons for pausing the medicament delivery process is not exhaustive and that there may be other reasons for a user desiring to pause the medicament delivery process after it has been initiated.

One or more aspects of the present disclosure allow the medicament delivery process to be paused and resumed by a user.

To pause the medicament delivery process after it has been initiated, the user may remove the medicament delivery device 200 from the injection site. FIG. 3C shows the medicament delivery device 200 of FIG. 3B in a paused state, after it has been removed from the injection site. The user has moved the body 111 away from the injection site, causing the needle cover 113 to translate axially with respect to the body 111 in a distal direction due to the biasing force applied by the needle cover biasing member 118.

Figure 3C:
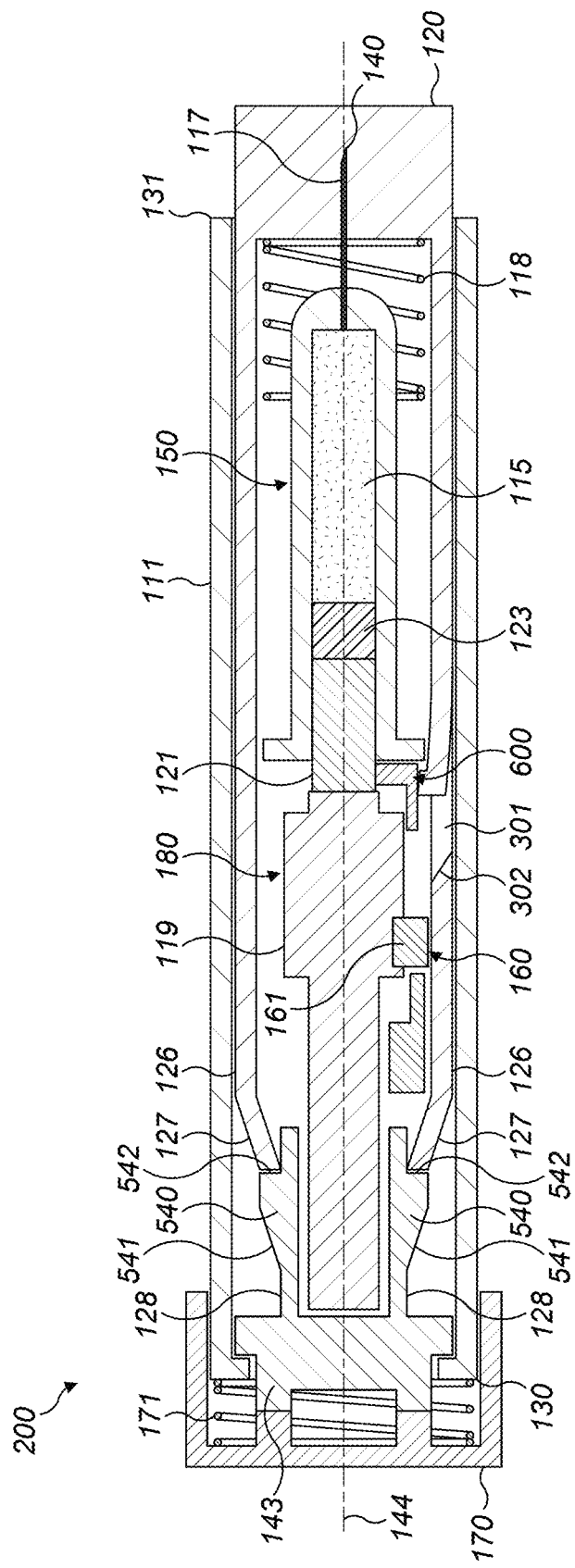
FIG. 3C is a schematic cross-sectional view of the medicament delivery device of FIG. 3B, in a paused state.
Figure 3D:
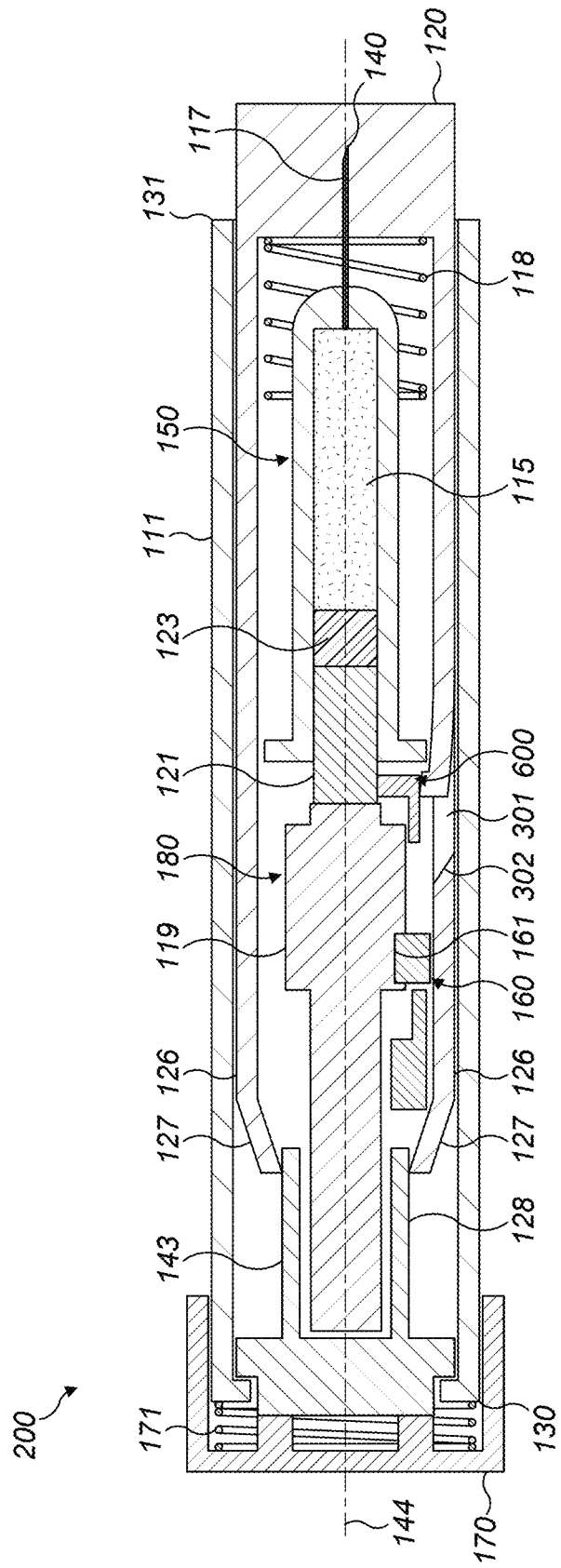
FIG. 3D is a schematic cross-sectional view of the medicament delivery device of FIG. 3C, in a resetting state.

Distal movement of the needle cover 113 relative to the body 111 from the retracted position shown in FIG. 3B towards the extended position shown in FIG. 3C has paused the medicament delivery process. That is, distal movement of the needle cover 113 from the retracted position towards the extended position has moved the latch 160 from the disengaged configuration shown in FIG. 3B, in which delivery of the medicament 115 by the medicament delivery mechanism 180 is allowed, to the engaged configuration shown in FIG. 3C, in which delivery of the medicament 115 by the medicament delivery mechanism 180 is inhibited (e.g., prevented).

FIG. 4C shows a cross-section through portions of the needle cover 113, latch 160, collar 119 and plunger 121 of the medicament delivery device 200 when the medicament delivery device 200 is in its paused state shown in FIG. 3C. Distal movement of the needle cover 113 (i.e., along the axis 144, into the page) has brought the needle cover recess 301 out of alignment with the latch 160 to cause the latch 160 to move from its disengaged configuration shown in FIG. 4B to its engaged configuration shown in FIG. 4C. As the needle cover 113 has moved distally, the inner surface of the needle cover 113 has been bought back into contact with the flexible arm 162, urging the flexible arm 162 to move radially inwards such that the engaging element 161 (e.g., protrusion) engages the collar 119.

The needle cover recess 301 may have a ramped side wall 302 (shown in FIGS. 3B and 3C) located at a proximal end of the recess 301 that is configured to engage the flexible arm 162 as the needle cover 113 moves distally, to assist with moving the flexible arm 162 radially inwards.

Engagement of the latch 160 with the collar 119 prevents further rotation of the collar 119 under the bias of the drive member, thereby pausing delivery of the medicament 115. As shown in FIG. 4C, radial movement of the flexible arm 162 has caused the engaging element 161 (e.g., protrusion) of the latch 160 to engage the engaging element 192 of the collar 119 to prevent rotation of the collar 119. The engaging element 192 of the collar 119 may be the same engaging element 192 previously discussed in relation to FIG. 4A with which the engaging element 161 of the latch 160 was previously engaged, or it may be a different engaging element 192 of the collar 119 (e.g., where the collar 119 comprises a plurality of engaging elements 192 arranged around its circumferential outer surface, and the collar 119 is in a different rotational alignment with the latch 160 due to the medicament delivery process).

As the needle cover 113 has moved distally from the retracted position (shown in FIG. 3B) to the extended position (shown in FIG. 3C), the projection 127 has travelled distally from the second position 502 in the second region 512 of the track 128 to the third position 503 in the third region of the track 503. During this movement, the projection 127 has moved over the locking element 540, with the projection 127 traversing in a distal and radial direction up the ramped surface 541 of the locking element 540 until it passes the locking surface 542.

Figure 5C:
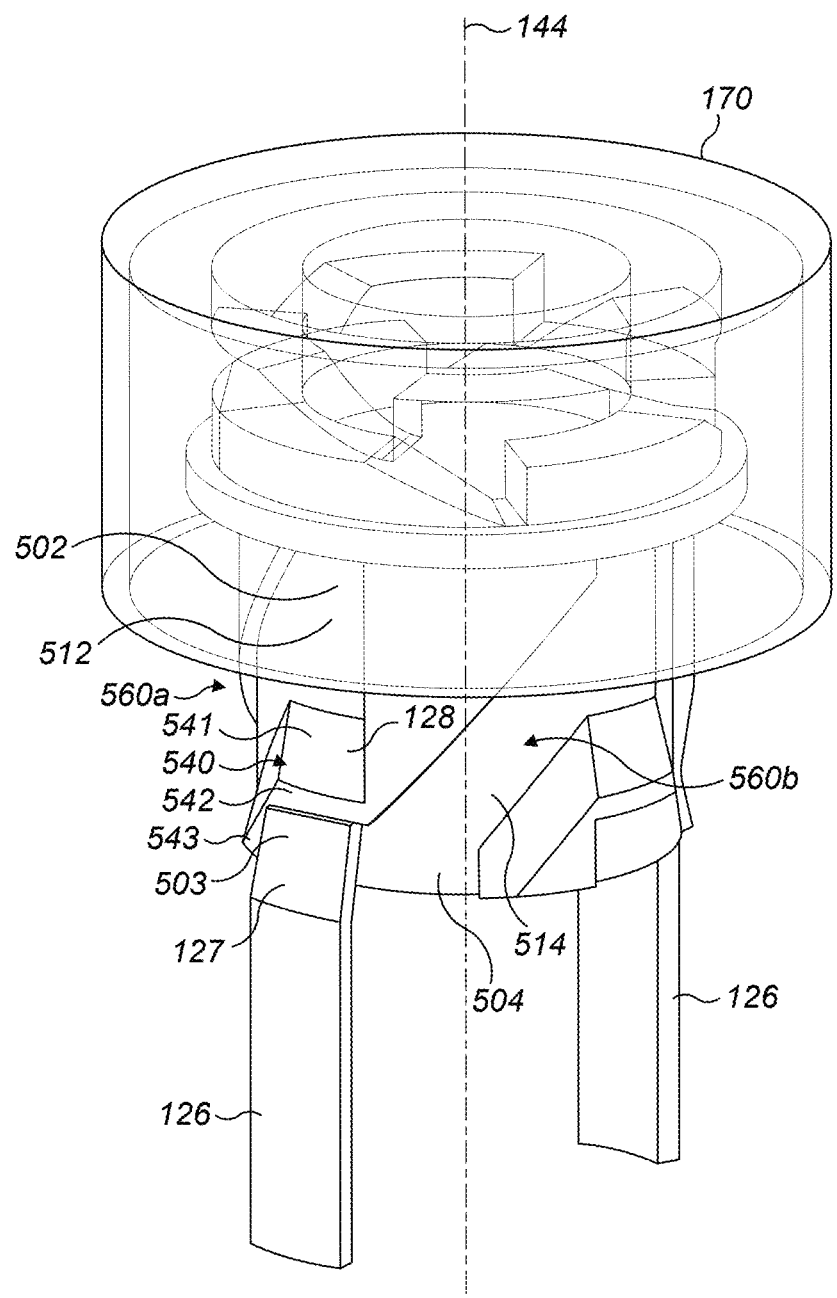
FIG. 5C is a partial perspective view of the needle cover guide, needle cover and actuation member of the medicament delivery device of FIG. 3C.

FIG. 5C shows the needle cover guide 143, needle cover 113 and actuation member 170 in a third configuration, corresponding to their configuration in FIG. 3C. As the projection 127 has traversed the ramped surface 541 of the locking element 540, it has been moved radially outwards due to flexibility of the arm 126 and/or projection 127. Once the projection 127 has moved distally to the locking surface 541, the projection 127 is no longer engaged by the ramped surface 541 and so now moves radially inwards, due to resiliency of the arm 126 and/or projection 127. Proximal movement of the needle cover 113 is now limited (i.e., prevented) by engagement between the projection 127 (or a different part of the arm 126) and the locking surface 542, as shown in FIG. 5C. This temporary 'locking' of the needle cover 113 to prevent further proximal movement may be beneficial in that it protects the distal end 140 of the needle 117 from being exposed to the user and/or subject after the needle cover 113 has moved back to its extended position, lessening the possibility of an accidental needle-stick event.

Rotation of the needle cover guide 143 relative to the needle cover 113 allows the needle cover 113 to be 'unlocked' such that it can be moved proximally again, from its extended position to its retracted position. Such rotation of the needle cover guide 143 may be performed using the actuation member 170.

FIG. 3D shows the medicament delivery device 200 of FIG. 3C in a resetting state, wherein the actuation member 170 has been actuated by a user to rotate the needle cover guide 143 relative to the needle cover 113. To actuate the actuation member 170, the user has applied a distal force to a proximally-facing surface of the actuation member 170 (e.g., by pressing the proximally-facing surface with a thumb or finger) to move the actuation member 170 distally, against the biasing force of the spring 171.

Figure 5D:
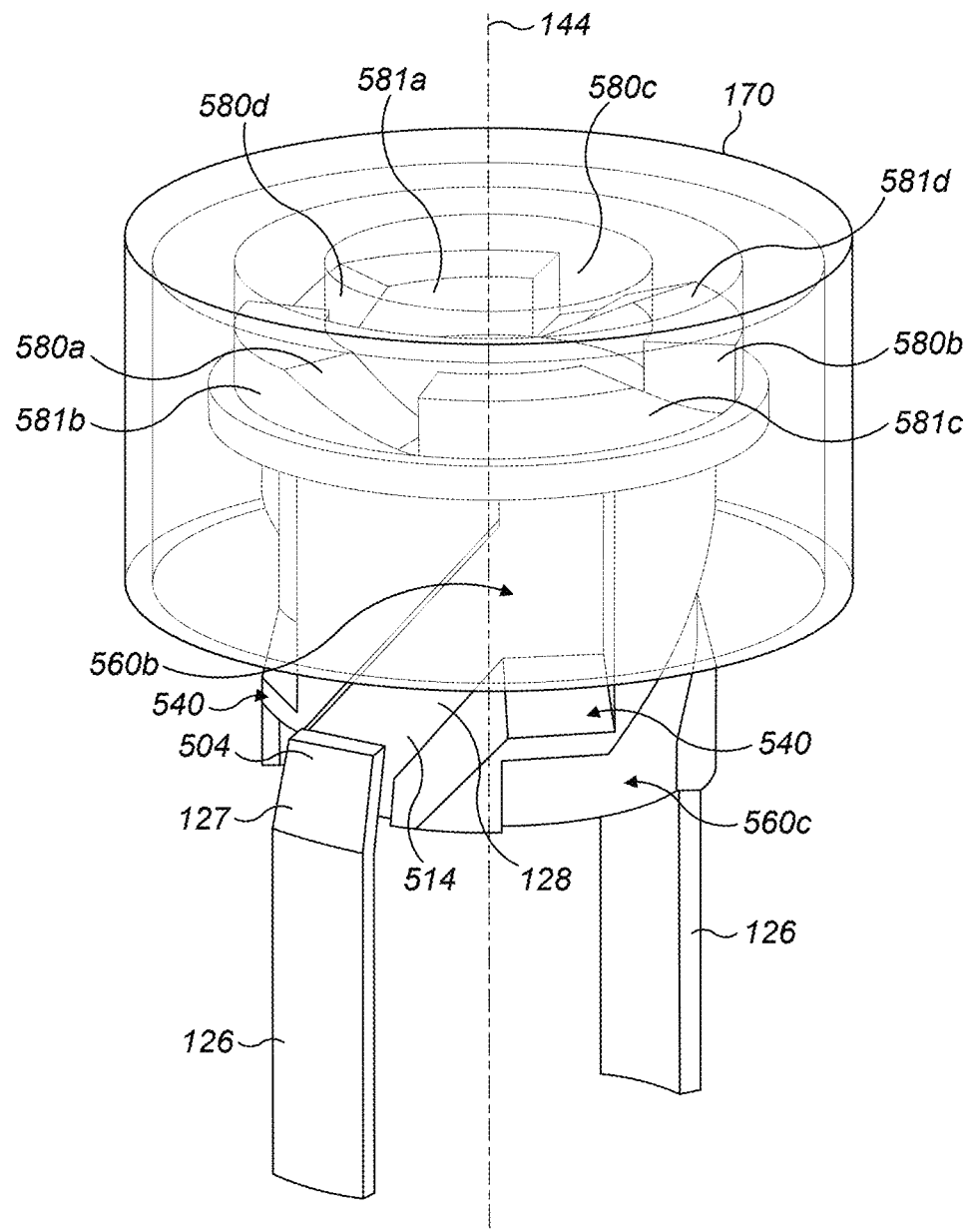
FIG. 5D is a partial perspective view of the needle cover guide, needle cover and actuation member of the medicament delivery device of FIG. 3D, during actuation of the actuation member.

FIG. 5D shows the needle cover guide 143, needle cover 113 and actuation member 170 in a third configuration, corresponding to their configuration in FIG. 3D. Distal axial movement of the actuation member 170 by the user from its first position (shown in FIG. 5C) to its second position (shown in FIG. 5D) has caused the needle cover guide 143 to be rotated as indicated by the arrow 520, due to engagement between the engagement elements 580a-580d of the actuation member and the respective engagement elements 581a-581d of the needle cover guide 143. More specifically, as the actuation member 170 has been moved from its first axial position towards its second axial position, engagement between each of the ramped surfaces 582a-582d of the actuation member 170 and corresponding ramped surfaces 583a-583d of the needle cover guide 143 has converted the axial movement of the actuation member 170 into rotation of the needle cover guide 143.

As shown in FIG. 5D, rotation of the needle cover guide 143 by the actuation member 170 has caused the protrusion 127 to travel from the third position 503 in the third region 513 to the fourth position 504 in the fourth region 514, such that proximal movement of the needle cover 113 from the extended position to the retracted position is no longer limited by the locking element 540.

Figure 5E:
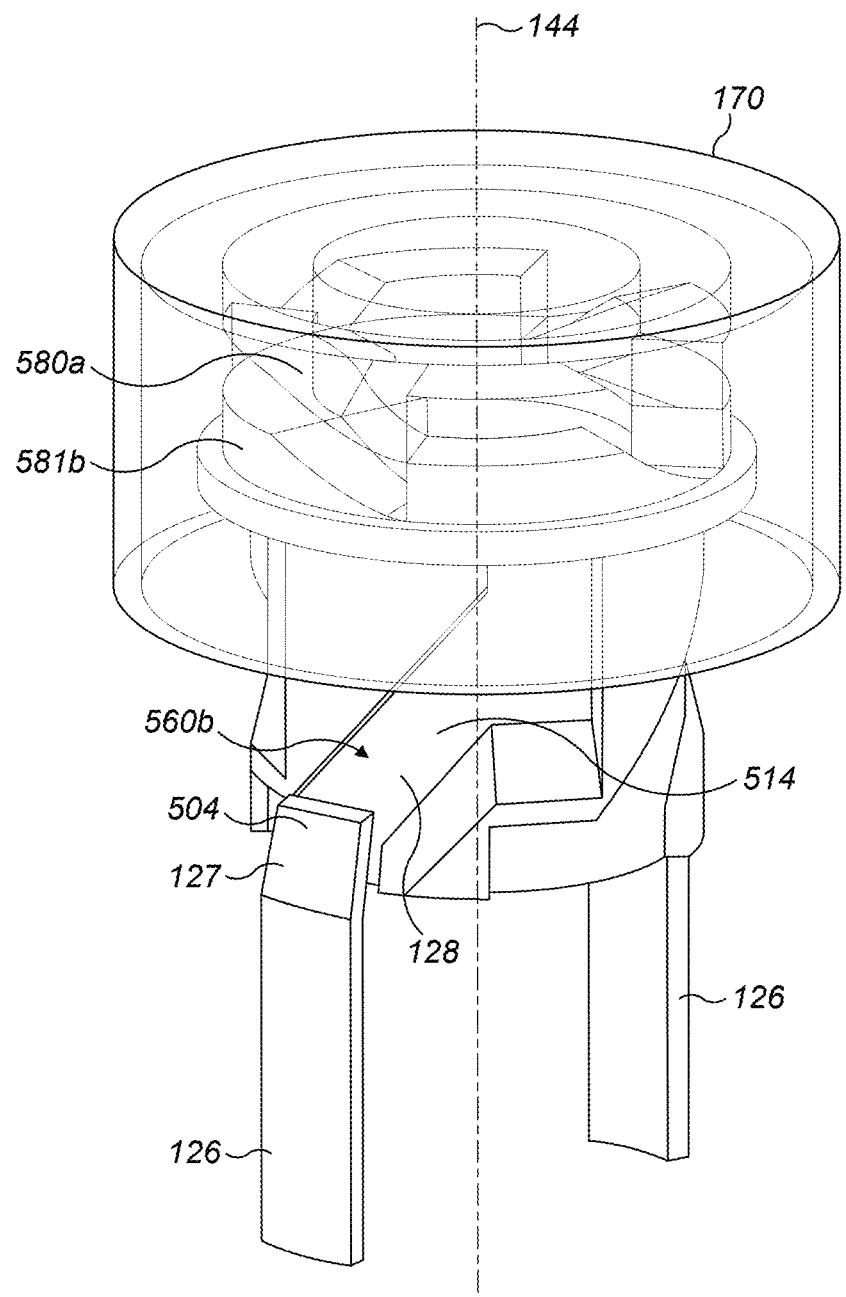
FIG. 5E is a partial perspective view of the needle cover guide, needle cover and actuation member of the medicament delivery device of FIG. 5D, after release of the actuation member.

FIG. 5E shows the needle cover guide 143, needle cover 113 and actuation member 170 in a fourth configuration, after the user has the user has released the actuation member 170 such that it has moved proximally relative to the needle cover guide 143 from its second position (shown in FIG. 5D) to its first position (shown in FIG. 5E), due to the biasing force of the spring 171. The engagement elements 580a-580d of the actuation member 170 have been brought out of engagement with the engagement elements 581a-581d of the needle cover guide 143. Distal axial movement of the actuation member 170 by the user from its first position back to its second position has not caused the needle cover guide 143 to be rotated any further.

As shown in FIG. 3D, the needle cover lock 600 remains in its initial configuration, in which movement of the needle cover 113 from the extended position to the retracted position is not limited by the needle cover lock 600. Furthermore, proximal movement of the needle cover 113 from the locked position to the retracted position is no longer limited by the needle cover guide 143 after rotation of the needle cover guide 143 using the actuation member 170. Therefore, the needle cover 113 is now free to move proximally to resume medicament delivery.

Figure 3E:
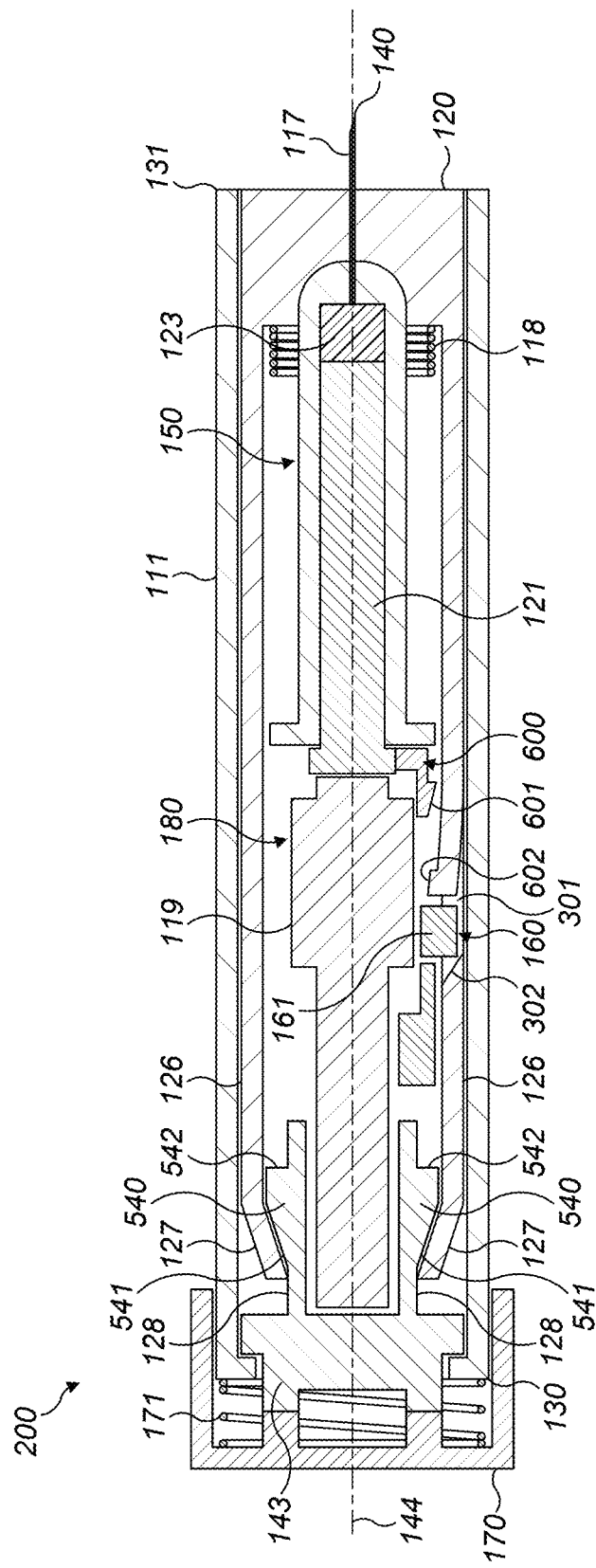
FIG. 3E is a schematic cross-sectional view of the medicament delivery device of FIG. 3D, in an resumed state.

FIG. 3E shows the medicament delivery device 200 of FIG. 3E after the medicament delivery process has been resumed.

The user may wish to resume the medicament delivery process to deliver one or more remaining portions of the medicament 115 to the same subject, for example because the subject is no longer experiencing discomfort, because the dosage regimen requires delivery of the medicament in a plurality of discrete doses, and/or because the medicament delivery device 200 has been moved from an incorrect injection site to a correct injection site. Alternatively, the user may wish to resume the medicament delivery process to deliver one or more remaining portions of the medicament 115 to a different subject.

In some examples, if the needle 117 can be uncoupled from the syringe 150, the user may replace the needle 117 of the medicament delivery device 200 with a new needle 117 prior to resuming the medicament delivery process. This may be performed for reasons of sterility, to prevent cross-contamination, and/or because the previous injection may have blunted the original needle 117. However, it should be understood that in other examples the needle 117 is not removed or replaced between injections.

FIG. 3E shows the medicament delivery device 200 of FIG. 3D now in a resumed state, which may be similar to the holding configuration discussed in relation to FIG. 3B, however the needle cover guide 143 has been rotated compared to the holding configuration.

As shown in FIG. 3E, the needle cover 113 has again been moved axially in a proximal direction with respect to the body 111. The needle cover 113 is shown in its retracted position, in which the distal end 140 of the needle 117 extends distal to the distal end 120 of the needle cover 113. The user has placed the distal end 120 of the needle cover 113 against an injection site (which may be the same injection site as before, or a different injection site) and moved the body 111 towards the injection site, causing the needle cover 113 to move proximally towards its retracted position and allowing the distal end 140 of the needle 117 to penetrate the injection site.

As the needle cover 113 is moved proximally, the latch 160 has again moved from its engaged configuration to its disengaged configuration, bringing the latch 160 out of engagement with the collar 119 of the medicament delivery mechanism 180 and thereby allowing the dispensing of the remaining medicament 115 to be resumed.

FIG. 3E shows that proximal movement of the needle cover 113 has again brought the recess 301 in the needle cover 113 into alignment with the latch 160 such that the latch 160 moves from its engaged configuration to its disengaged configuration with respect to the collar 119. The latch 160 will be in a similar disengaged configuration as previously described in relation to FIG. 4B. Disengagement of the latch 160 from the collar 119 has allowed the collar 119 to be rotated by the drive member and, through interaction between the collar 119 and the plunger 121, caused the plunger 121 to again move axially in a distal direction to move the piston 123 distally to dispense at least a portion of the remaining medicament 115 (e.g., in a similar manner as previously described in relation to FIG. 4B).

It can be seen in FIG. 3E that movement of the needle cover 113 from the extended position to the retracted position has again caused the needle cover guide 143 to be rotated, in a similar manner as described in relation to FIGS. 5A and 5B. Proximal movement of the needle cover 113 and rotation of the needle cover guide 143 has moved the locking element 540 relative to the projection 127 such that it is now distal to the projection 127 and axially aligned relative to the projection 127. The locking element 540 which may be the same locking element 540 as FIG. 3C if the track 128 comprises a single portion 560, or else a different locking element 540 from an adjacent/subsequent portion 560 of the track 128 if the track 128 comprises more than one portion 560.

The needle cover lock 600 remains in its initial configuration until the medicament delivery process is complete. While the needle cover lock 600 remains in its initial configuration, the user may once again pause the medicament delivery process by removing the medicament delivery device 200 from the injection site and causing the latch 160 to move to its engaged configuration, as described previously. To resume medicament delivery, the user rotates the needle cover guide 143 by actuating the actuation member 170 as described previously, before pressing the medicament delivery device 200 against the injection site to move the latch 160 to its disengaged configuration. The process of pausing and resuming medicament delivery may be repeated multiple times until the medicament delivery process is complete (e.g., after the medicament 115 has been fully dispensed), with the user actuating the actuation member 170 after each pause in the medicament delivery process so that the medicament delivery process can be resumed.

Once the delivery of medicament is complete, the needle cover lock 600 is moved to its locking configuration as shown in FIG. 3E, wherein movement of the needle cover 113 from the extended position to the retracted position is limited by the needle cover lock 600 when in the locking configuration. When in the locking configuration, a projection 601 of the needle cover lock 600 is able to engage an engaging element 602 of the needle cover 113 to limit proximal movement of the needle cover 113. FIG. 3E shows the projection 601 of the needle cover lock 600 has been moved into position by the plunger 121 but is not yet engaged with the engaging element 602 of the needle cover 113 to inhibit proximal movement of the needle cover 113.

Figure 3F:
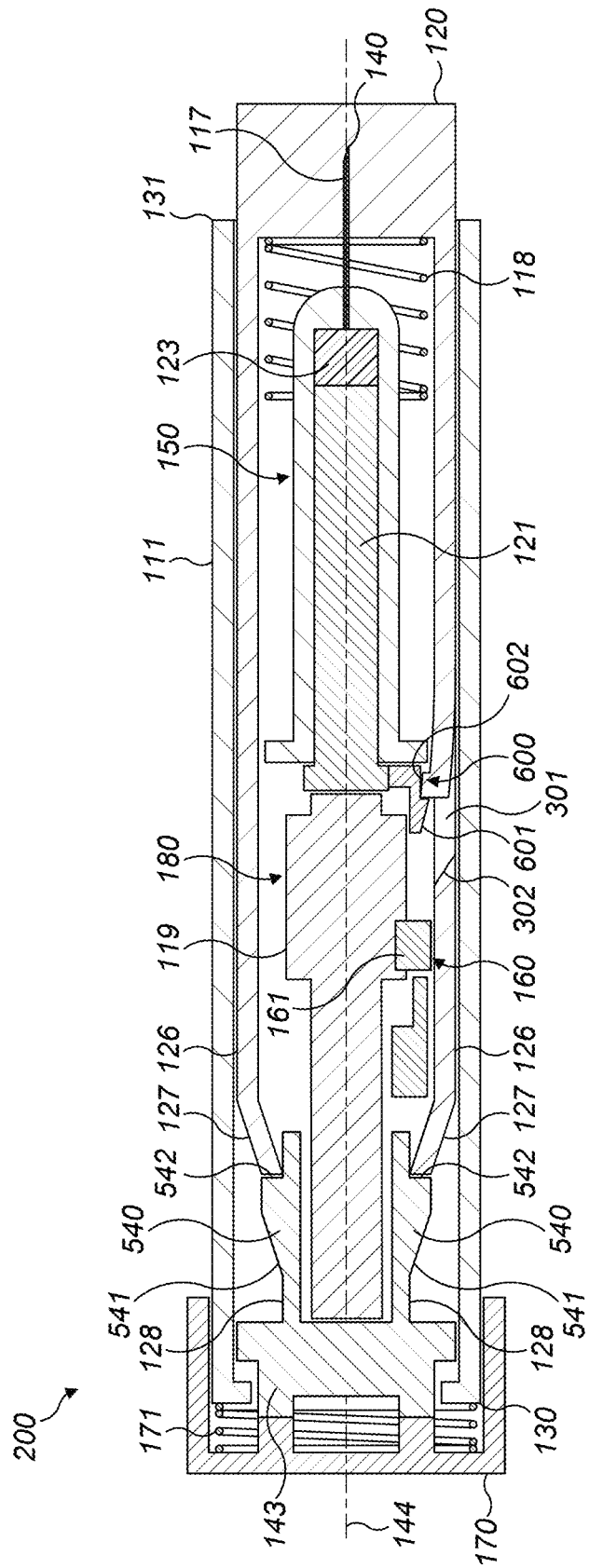
FIG. 3F is a schematic cross-sectional view of the medicament delivery device of FIG. 3E, in a locked state.

FIG. 3F shows the medicament delivery device 200 of FIG. 3E in a locked state after the medicament delivery process is complete.

FIG. 3F shows the medicament delivery device 200 of FIG. 3E after the needle cover lock 600 has been moved into its locking configuration by the plunger 121 and the medicament delivery device 200 has been removed from the injection site. The user has moved the body 111 away from the injection site, causing the needle cover 113 to translate axially with respect to the body 111 in a distal direction due to the biasing force applied by the needle cover biasing member 118. As the needle cover 113 has moved to the extended state, the projection 601 of the needle cover lock 600 has engaged the engaging element 602 of the needle cover 113 to lock the needle cover 113 relative to the body 111 and limit subsequent proximal movement of the needle cover 113. As such, the medicament delivery device 200 can no longer be used for medicament delivery and can now be disposed of safely.

FIGS. 6A-6D are schematic partial side-views of the medicament delivery device 200 of FIGS. 3A-3F, showing various operations of the needle cover lock 600 in greater detail. FIGS. 6A-6D show only portions of the needle cover 113, needle cover lock 600 and the plunger 121. One or more other features of the medicament delivery device 200 are hidden for improved clarity.

Figure 6A:
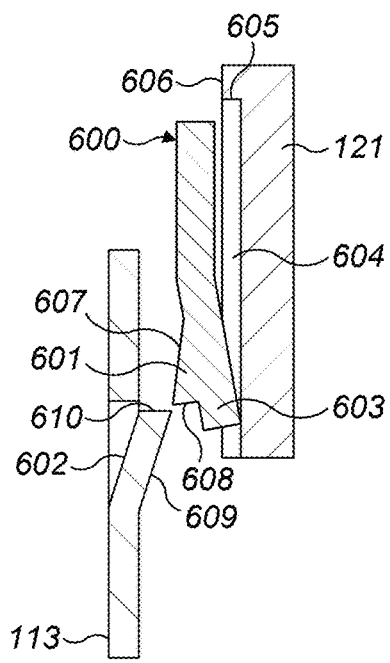
FIG. 6A is a schematic partial side view of the medicament delivery device of FIG. 3A, showing a needle cover lock in an initial configuration and the needle cover in an extended position.

FIG. 6A shows the needle cover lock 600 in its initial configuration, corresponding to the medicament delivery device 200 being in its initial state shown in FIG. 3A. The needle cover 113 is in its extended position and the plunger 121 has not yet been moved axially by the collar 119. The needle cover lock 600 comprises a flexible arm 603 having a projection 601 arranged at a free end, which extends radially outwards. When the needle cover lock 600 is in its initial configuration, the projection 601 does not engage the engaging element 602 formed at the inner surface of the needle cover 113 and so does not limit proximal movement of the needle cover 113. FIG. 6A shows the arm 603 at least partially received within a recessed portion 604 of the plunger 121. The flexible arm 603 may be biased into this position (e.g., due to resiliency of the flexible arm 603). The engaging element 602 is located distal to the projection 601.

Figure 6B:
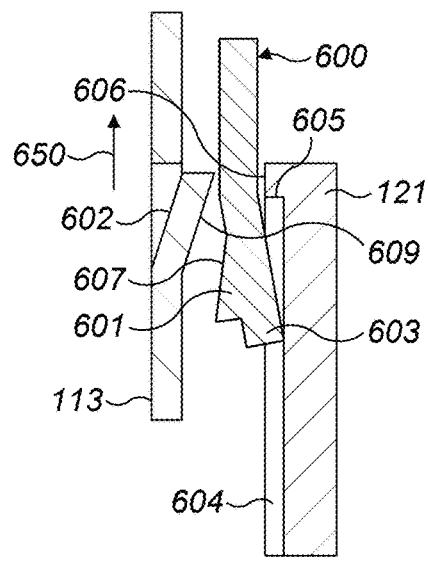
FIG. 6B is a schematic partial side view of the medicament delivery device of FIG. 3B, showing the needle cover lock in the initial configuration and the needle cover in a retracted position.

FIG. 6B shows the needle cover lock 600 while the medicament delivery device 200 is in its holding state shown in FIG. 3B, wherein the needle cover lock 600 remains in its initial configuration. The needle cover 113 has moved proximally from its extended position to its retracted position, as indicated by arrow 650, such that the engaging element 602 is now located proximal to the projection 601. The plunger 121 has been moved distally by the collar 119, by a distance corresponding to a partial delivery of the medicament 115. The arm 603 remains at least partially received with the recessed portion 604 of the plunger 121, with the arm 603 and the projection 601 having not substantially moved position. The projection 601 does not engage the engaging element 602 formed at the inner surface of the needle cover 113 and so does not limit proximal movement of the needle cover 113.

Figure 6C:
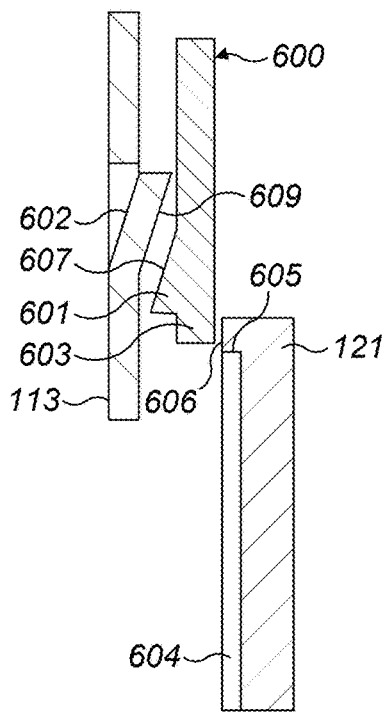
FIG. 6C is a schematic partial side view of the medicament delivery device of FIG. 3E, showing the needle cover lock in a locking configuration and the needle cover in the retracted position.

FIG. 6C shows the needle cover lock 600 while the medicament delivery device 200 is in its resumed state shown in FIG. 3E, wherein the medicament delivery process is complete. The needle cover 113 has remained in its retracted position, however the medicament delivery mechanism 180, and in particular the plunger 121, has moved the needle cover lock 600 from its initial configuration (shown in FIG. 6B) to its locking configuration (shown in FIG. 6C). More specifically, the plunger 121 has continued to be moved distally due to rotation of the collar 119, causing the arm 603 of the needle cover lock 600 to traverse the recessed portion 604 of the plunger 121 until it reaches a proximal side wall 605 of the recessed portion 604. Once the arm 603 has reached the proximal side wall 605, continued distal movement of the plunger 121 causes the flexible arm 603 and the projection 601 to be pushed radially outwards by engagement between a raised surface 606 of the plunger 121 and the arm 603, wherein the raised surface 606 is located proximal to the recessed portion 604 on the plunger 121. The needle cover lock 600 is held in its locking configuration by the raised surface 606 of the plunger 121. The proximal side wall 605 and raised surface 606 may be arranged on the plunger 121 such that they engage to move the needle cover lock 600 into the locking configuration once delivery of the medicament is complete, or shortly before delivery of the medicament is complete.

Figure 6D:
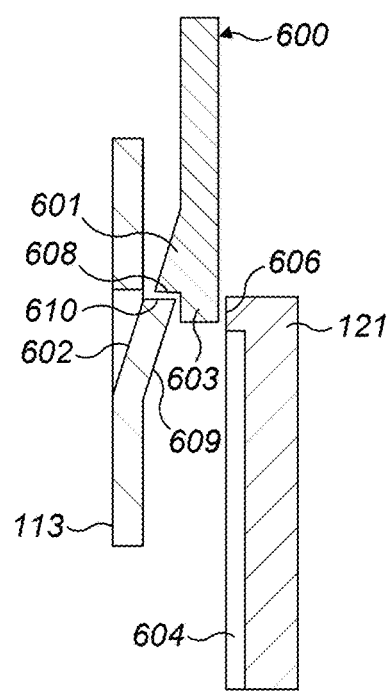
FIG. 6D is a schematic partial side view of the medicament delivery device of FIG. 3F, showing the needle cover lock in the locking configuration and the needle cover in the extended position.

FIG. 6D shows the needle cover lock 600 while the medicament delivery device 200 is in its locked state shown in FIG. 3F. The needle cover 113 has moved distally from its retracted position to its extended position, causing the engaging element 602 to move distally relative to the projection 601 until it engages the projection 601. As the engaging element 602 moves distally, a distally-facing ramped surface 609 of the engaging element 602 is brought into engagement with a proximally-facing ramped surface 607 of the projection 603. Continued distal movement of the engaging element 602 causes the distally-facing ramped surface 609 of the engaging element 602 to slide over the proximally-facing ramped surface 607 of the projection 603, with interaction between the ramped surfaces 609, 607 causing the engaging element 602 to move radially outwards and/or the projection 601 to be moved radially inwards (due to flexing of the engaging element 602, needle cover 113, projection 601 and/or flexible arm 603). Once a blocking surface 608 of the projection 601 passes a blocking surface 610 of the engaging element 602, the engaging element 602 moves radially inwards and/or the projection 601 moves radially outwards. The blocking surface 608 of the projection 601 now engages the blocking surface 610 of the engaging element 602 such that proximal movement of the needle cover 113 to uncover the needle 117 is now limited (i.e., prevented).

It has been generally been described throughout this disclosure that the or each flexible arm 126 has a protrusion 127 which engages the track 128. However, it should be noted that in some examples, the or each flexible arm 126 does not have a protrusion 127 which engages the track 128. Instead, for example, a surface of the flexible arm(s) 126 could engage the track 128.

In any of the embodiments disclosed herein, the medicament delivery device 200 may additionally have a cap 12 which covers the distal end of the needle cover 113. The cap 12 may be coupled to the remainder of the medicament delivery device 200 (e.g., to the body 111) when the medicament delivery device 100 is in its initial state corresponding to FIG. 3A. The cap 12 may be removed from the remainder of the medicament delivery device 200 by the user, prior to injection. Removal of the cap 12 may also remove a rigid needle shield (RNS) surrounding the needle 117, wherein the RNS is removed with the cap 12 (e.g., due to engagement between the RNS and the cap 12).

Figure 7:
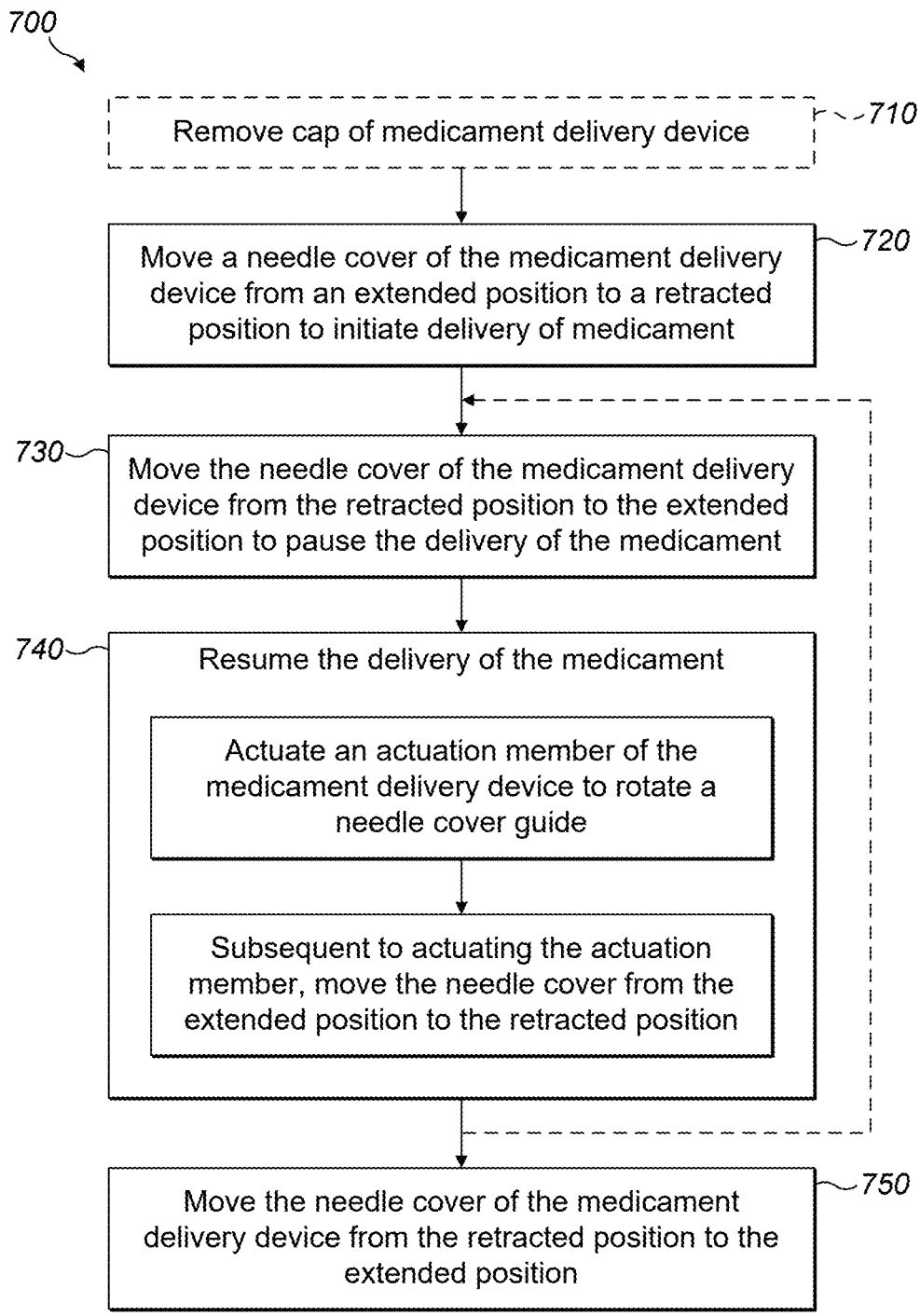
FIG. 7 is a flowchart illustrating a method of using a medicament delivery device in accordance with one or more aspects.

A method 700 of using a medicament delivery device, which may be the medicament delivery device 200 described in relation to FIGS. 3A-3F, will now be described with reference to FIG. 7.

At optional operation 710 of the method 700, a cap 12 of the medicament delivery device is removed (if present).

At operation 720, a needle cover 113 of the medicament delivery device is moved from an extended position to a retracted position to initiate delivery of a medicament 115 by a medicament delivery mechanism 180 of the medicament delivery device (e.g., as previously described herein). The needle cover 113 may be moved from the extended position to the retracted position by pressing the needle cover 113 against an injection site.

At operation 730, the needle cover 113 of the medicament delivery device is moved from the retracted position to the extended position to pause the delivery of the medicament 115 by the medicament delivery mechanism 180 (e.g., as previously described herein). The needle cover 113 may be moved from the retracted position to the extended position by removing the needle cover 113 from the injection site. The medicament delivery mechanism 180 may have delivered only a portion of the medicament 115 held within the medicament delivery device when the delivery was paused.

At operation 740, the delivery of the medicament 115 by the medicament delivery mechanism 180 is resumed (e.g., as previously described herein). To resume the medicament delivery, the user may first actuate an actuation member 170 of the medicament delivery device to rotate a needle cover guide 143, before moving the needle cover 113 from the extended position to the retracted position (e.g., by pressing the needle cover 113 against the injection site, or a different injection site). The medicament delivery mechanism may continue delivering the remaining medicament 115.

Optionally, operations 730 and 740 may be repeated multiple times in order to pause and resume the delivery of the medicament multiple times.

Once medicament delivery is complete, at operation 750, the needle cover 113 of the medicament delivery device is moved from the retracted position to the extended position (e.g., by removing the needle cover 113 from the injection site). As the needle cover 113 is moved from the retracted position to the extended position, a needle cover lock prevents subsequent proximal movement of the needle cover 113.

While various aspects of this disclosure have been described as suitable for pausing and resuming the delivery of a medicament such that the medicament may be delivered in a plurality of discrete doses, it should be understood that aspects of this disclosure may additionally/alternatively be used to pause and resume a medicament delivery process prior to any medicament being dispensed. For example, in accordance with one or more aspects of this disclosure, a user may initiate movement of the medicament delivery mechanism by pushing the medicament delivery device into an injection site, but may remove the medicament delivery device from the injection site prior to actual dispensing of any medicament (e.g., before the plunger has contacted the piston). Thus, no medicament is actually injected into the subject. Such a feature may be useful where the user has inserted the needle at an inappropriate injection site, since it allows the user to move the medicament delivery device to a correct injection site before any medicament is actually dispensed.

While various aspects of this disclosure describe the use of an actuation member 170 to rotate the needle cover guide 143, it should be noted that alternative methods of rotating the needle cover guide 143 to allow for proximal movement of the needle cover 113 could be employed. For example, in some embodiments at least a portion of the needle cover guide 143 may be accessible to the user from outside the body 111 such that the user may rotate the needle cover guide 143 by directly touching and rotating the needle cover guide 143 (e.g., without the use of an actuation member 170).

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrom.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present disclosure, which encompass such modifications and any and all equivalents thereof.

LIST OF REFERENCE NUMBERS

10—drug delivery device
11—housing
11a—window
12—cap assembly
13—needle sleeve
14—reservoir
15—medicament
17—needle 20—distal region
21—proximal region
22—button
23—bung or piston
100—medicament delivery device
111—body
113—needle cover
114—container
115—medicament
117—needle
118—needle cover biasing member
119—collar
120—distal end (of the needle cover)
121—plunger
122—external screw thread
123—bung or piston
124—drive member
126—arm
127—protrusion (of needle cover guide)
128—track
130—proximal end (of body)
131—distal end (of body)
140—distal end (of needle)
142—arrow
143—needle cover guide
144—axis
150—syringe
160—latch
161—engaging element (of latch)
162—flexible arm (of latch)
166—side wall (of engaging element of latch)
170—actuation member
171—spring
180—medicament delivery mechanism
191—engaging element (of collar)
196—side wall (of engaging element of collar)
200—medicament delivery device
301—needle cover recess
302—ramped side wall
501—first position (of track)
502—second position (of track)
503—third position (of track)
504—fourth position (of track)
511—first region (of track)
512—second region (of track)
513—third region (of track)
514—fourth region (of track)
520—arrow
521—arrow
530—proximal side wall (of first region)
540—locking element (of track)
541—ramped surface (of locking element)
542—locking surface (of locking element)
543—side wall (of third region)
560a-560d—portions (of track)
580a-580d—engagement elements (of actuation member)
581a-581d—engagement elements (of needle cover guide)
582a-582d—ramped surfaces
583a-583d—ramped surfaces
600—needle cover lock
601—projection (of needle cover lock)
602—engaging element (of needle cover)
603—flexible arm (of needle cover lock)
604—recessed portion (in plunger)
605—proximal side wall (of recessed portion)
606—raised surface (of plunger)
607—ramped surface (of needle cover lock)
608—blocking surface (of needle cover lock)
609—ramped surface (of engaging element of needle cover)
610—blocking surface (of engaging element of needle cover)
650—arrow
700—method
710—operation
720—operation
730—operation
740—operation
750—operation

The invention claimed is:

1. A medicament delivery device comprising:
a needle for injecting a medicament;
a body having a proximal end and a distal end;
a needle cover axially movable relative to the body between an extended position, in which a distal end of the needle cover is distal to a distal end of the needle, and a retracted position, in which the distal end of the needle is distal to the distal end of the needle cover;
a needle cover biasing member configured to bias the needle cover distally;
a medicament delivery mechanism; and
a latch movable by the needle cover between an engaged configuration, in which the latch is engaged with a component of a medicament delivery mechanism to prevent delivery of the medicament, and a disengaged configuration, in which the latch is disengaged from the component of the medicament delivery mechanism to allow delivery of the medicament,
wherein the needle cover is configured such that:
proximal movement of the needle cover from the extended position towards the retracted position moves the latch from the engaged configuration to the disengaged configuration; and
distal movement of the needle cover from the retracted position towards the extended position moves the latch from the disengaged configuration to the engaged configuration, and
wherein the latch comprises an engaging element configured to:
engage an engaging element of the component of the medicament delivery mechanism when the latch is in the engaged position; and
be disengaged from the engaging element of the component when the latch is in the disengaged position.

2. The medicament delivery device according to claim 1, wherein the latch is movable between the engaged position and the disengaged position a plurality of times for pausing and resuming delivery of the medicament a plurality of times.

3. The medicament delivery device according to claim 1, further comprising a needle cover guide comprising a track, wherein the needle cover comprises an arm configured to engage the track such that a proximal movement of the needle cover is limited after the needle cover has moved from the retracted position to the extended position.

4. The medicament delivery device according to claim 3, wherein the needle cover guide is rotatable relative to the body, and wherein the track extends at least partially around a circumference of the needle cover guide for rotating the needle cover guide as the needle cover moves from the extended position to the retracted position.

5. The medicament delivery device according to claim 3, wherein the arm comprises a protrusion configured to engage the track.

6. The medicament delivery device according to claim 5, wherein the track comprises a first region and a second region, wherein the protrusion travels from the first region to the second region as the needle cover moves from the extended position to the retracted position.

7. The medicament delivery device according to claim 6, wherein:
the track comprises a third region,
the protrusion travels from the second region to the third region as the needle cover moves distally from the retracted position to the extended position, and
the third region comprises a locking element configured to limit proximal movement of the needle cover when the needle cover is in the extended position.

8. The medicament delivery device according to claim 7, wherein the locking element comprises a locking surface configured to be engaged by the needle cover when the needle cover is in the extended position to limit proximal movement of the needle cover.

9. The medicament delivery device according to claim 7, wherein the track further comprises a fourth region, wherein the protrusion travels from the third region to the fourth region as the needle cover guide is rotated, wherein proximal movement of the needle cover from the locked position to the retracted position is allowed when the protrusion is in the fourth region.

10. The medicament delivery device according to claim 9, further comprising an actuation member, wherein the actuation member is actuatable by a user to rotate the needle cover guide relative to the needle cover such that the protrusion travels from the third region to the fourth region.

11. The medicament delivery device of claim 10, wherein the actuation member comprises a button arranged at a proximal end of the medicament delivery device.

12. The medicament delivery device of claim 1, wherein the engaging element of the latch comprises a projection and the engaging element of the component comprises a recess.

13. The medicament delivery device according to claim 1, wherein the component of the medicament delivery mechanism is a collar that is rotatable relative to the body to dispense the medicament, wherein the latch is configured to engage the collar when in the engaged position to limit rotation of the collar.

14. The medicament delivery device according to claim 1, wherein the latch is biased from the engaged configuration to the disengaged configuration, wherein the latch is held in the engaged position by the needle cover when the needle cover is in the extended position, and wherein the needle cover comprises a recess configured to receive at least a portion of the latch when the needle cover is in the retracted position such that the latch can move to the disengaged position.

15. The medicament delivery device according to claim 1, further comprising a needle cover lock that is movable by the medicament delivery mechanism between an initial configuration, in which movement of the needle cover from the extended position to the retracted position is not limited by the needle cover lock, and a locking position, in which movement of the needle cover from the extended position to the retracted position is limited by the needle cover lock.

16. The medicament delivery device of claim 15, wherein the needle cover lock is moved from the disengaged position to the engaged position by a plunger of the medicament delivery mechanism.

17. The medicament delivery device according to claim 1, further comprising the medicament.

18. A method of operating a medicament delivery device, the method comprising:
moving a needle cover of the medicament delivery device from an extended position to a retracted position to initiate delivery of a medicament;
moving the needle cover of the medicament delivery device from the retracted position to the extended position to pause the delivery of the medicament; and
resuming the delivery of the medicament by:
actuating an actuation member of the medicament delivery device to rotate a needle cover guide, wherein at least one of the actuation member or the needle cover guide comprises a ramped surface configured to convert linear movement of the actuation member into rotation of the needle cover guide; and
subsequent to actuating the actuation member, moving the needle cover from the extended position to the retracted position.

* * * * *